(12) United States Patent
Lee et al.

(10) Patent No.: US 9,587,261 B2
(45) Date of Patent: Mar. 7, 2017

(54) **MICROORGANISM OF THE GENUS *ESCHERICHIA* HAVING ENHANCED L-TRYPTOPHAN PRODUCTIVITY AND A METHOD FOR PRODUCING L-TRYPTOPHAN USING THE SAME**

(71) Applicant: CJ Cheiljedang Corporation, Seoul (KR)

(72) Inventors: Kwang Ho Lee, Seoul (KR); Hye Min Park, Gyeongsangnam-do (KR); Hyo Hyoung Lee, Incheon (KR); Young Bin Hwang, Seoul (KR); Seok Myung Lee, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 14/371,465

(22) PCT Filed: Jan. 10, 2013

(86) PCT No.: PCT/KR2013/000214
§ 371 (c)(1),
(2) Date: Jul. 10, 2014

(87) PCT Pub. No.: WO2013/105800
PCT Pub. Date: Jul. 18, 2013

(65) Prior Publication Data
US 2015/0147788 A1 May 28, 2015

(30) Foreign Application Priority Data
Jan. 10, 2012 (KR) .................. 10-2012-0002906
Jan. 10, 2013 (KR) .................. 10-2013-0002913

(51) Int. Cl.
| | | |
|---|---|---|
| C12P 13/22 | (2006.01) | |
| C12N 1/20 | (2006.01) | |
| C07K 14/245 | (2006.01) | |
| C12N 15/71 | (2006.01) | |
| H01L 27/32 | (2006.01) | |
| H01L 51/52 | (2006.01) | |

(52) U.S. Cl.
CPC .......... *C12P 13/227* (2013.01); *C07K 14/245* (2013.01); *C12N 15/71* (2013.01); *H01L 27/3276* (2013.01); *H01L 51/5231* (2013.01)

(58) Field of Classification Search
None
See application file for complete search history.

(56) References Cited

U.S. PATENT DOCUMENTS

| | | | |
|---|---|---|---|
| 4,371,614 A | 2/1983 | Anderson et al. | |
| 6,180,373 B1 * | 1/2001 | Wich ................. | C12P 13/22 435/108 |
| 2009/0239269 A1 | 9/2009 | Tajima et al. | |
| 2010/0028956 A1 * | 2/2010 | Ju ....................... | C12N 9/88 435/108 |

FOREIGN PATENT DOCUMENTS

| | | | |
|---|---|---|---|
| EP | 0 165 614 A2 | 12/1985 | |
| JP | S64-71478 A | 3/1989 | |
| JP | 2005-151829 A | 6/2005 | |
| KR | 10-2006-0101545 A | 9/2006 | |
| WO | WO 84/00380 A1 | 2/1984 | |
| WO | WO 8701130 A1 * | 2/1987 | ............ C12N 15/52 |
| WO | WO 2005/049808 A1 | 6/2005 | |

OTHER PUBLICATIONS

Miozzari et al., "Translation of the Leader Region of the *Escherichia coli* Tryptophan Operon", J. Bacteriol. 133:1457-1466, 1978.*
Landick et al., "Replacement of the *Escherichia coli* trp operon attenuation control codons alters operon expression", J. Mol. Biol. 216:25-37, 1990, Abstract.*
EMBL Accession No. V00372, Apr. 2005, 5 pages.*
Chen, J. W., et al. (1991) J. Bacteriol 173(7)2328, "Specificity of attenuation control in the ilvGMEDA operon of *Escherichia coli* K-12."
GenBank Accession #; J01714.1, Apr. 2002.
Park, E.,Y., et al. (2002) Biotechnology Letters 24 :1815-1819, "Removal attenuator region of *thr* operon increase the production of threonine in *Escherichia coli*."
International Search Report mailed May 30, 2013 in PCT/KR2013/000214.
Park et al. (2002) Biotechnology Letters 24:1815-1819, "Removal of attenuator region of *thr* operon increases the production of threonine in *Escherichia coli*".
Yanofsky (2007) RNA 13:1141-1154, "RNA-based regulation of genes of tryptophan synthesis and degradation, in bacteria".
European Search Report issued Mar. 4, 2016 in EP 13735653.1.
Database Geneseq [Online], Mar. 25, 2003, "trp Promoter of hybrid plasmid pTREZI.", XP002754727, retrieved from EBI accession No. GSN: AAN60352, Database accession No. AAN60352.
Database EMBL [Online], Jul. 15, 1993, "Nucleotide sequence 8 from patent No. WO8400380", XP002754728, retrieved from EBI accession No. EM_PAT:A04494, Database accession No. A04494.
Database EMBL [Online], Oct. 7, 1997, "DNA fragment of regulatory region at expression vector Ptrp ED5-1", XP002754729, retrieved from EBI accession No. EM_PAT:E01880 Database accession No. E01880.

* cited by examiner

*Primary Examiner* — David J Steadman
(74) *Attorney, Agent, or Firm* — Swanson & Bratschun, L.L.C.

(57) ABSTRACT

The present invention relates to microorganisms of *Escherichia coli* having enhanced L-tryptophan productivity and to a method for producing L-tryptophan using the same. More particularly, the present invention relates to an *Escherichia coli* variant in which repression and attenuation control of the tryptophan operon is released and accumulation of anthranilate is reduced and thereby enhancing L-tryptophan productivity. The present invention also relates to a method for producing L-tryptophan using the *Escherichia coli* variant.

7 Claims, 3 Drawing Sheets

SEQUENCE LISTING

```
<160> NUMBER OF SEQ ID NOS: 40

<210> SEQ ID NO 1
<211> LENGTH: 273
<212> TYPE: DNA
<213> ORGANISM: Escherichia coli

<400> SEQUENCE: 1
ggcgcactcc cgttctggat aatgtttttt gcgccgacat cataacggtt ctggcaaata     60
ttctgaaatg agctgttgac aattaatcat cgaactagtt aactagtacg caagttcacg    120
taaaaagggt atcgacaatg aaagcaattt tcgtactgaa aggttggtgg cgcacttcct    180
gaaacgggca gtgtattcac catgcgtaaa gcaatcagat acccagcccg cctaatgagc    240 gggcttttt ttgaacaaaa ttagagaata aca                                  273

<210> SEQ ID NO 2
<211> LENGTH: 45
<212> TYPE: DNA
<213> ORGANISM: Escherichia coli

<400> SEQUENCE: 2
atgaaagcaa ttttcgtact gaaaggttgg tggcgcactt cctga                     45

<210> SEQ ID NO 3
<211> LENGTH: 91
<212> TYPE: DNA
<213> ORGANISM: Escherichia coli

<400> SEQUENCE: 3
aacgggcagt gtattcacca tgcgtaaagc aatcagatac ccagcccgcc taatgagcgg     60
gctttttttt gaacaaaatt agagaataac a                                    91

<210> SEQ ID NO 4
<211> LENGTH: 14
<212> TYPE: PRT
<213> ORGANISM: Escherichia coli

<400> SEQUENCE: 4

Met Lys Ala Ile Phe Val Leu Lys Gly Trp Trp Arg Thr Ser
1               5                   10

<210> SEQ ID NO 5
<211> LENGTH: 245
<212> TYPE: DNA
<213> ORGANISM: Artificial Sequence
<220> FEATURE:
```

<223> OTHER INFORMATION: synthetic

<400> SEQUENCE: 5

| | | | | | |
|---|---|---|---|---|---|
| ttaggtaccg | gcgcactccc | gttctggata | atgttttttg | cgccgacatc | ataacggttc | 60 |
| tggcaaatat | tctgaaatga | gctgttgaca | attaatcatc | gaactagtta | actagtacgc | 120 |
| aagttcacgt | aaaagggta | tcgacaacgg | gcagtgtatt | caccatgcgt | aaagcaatca | 180 |
| gatacccagc | ccgcctaatg | agcgggcttt | ttttttgaaca | aaattagaga | ataacagata | 240 |
| tcatt | | | | | | 245 |

<210> SEQ ID NO 6
<211> LENGTH: 148
<212> TYPE: DNA
<213> ORGANISM: Artificial Sequence
<220> FEATURE:
<223> OTHER INFORMATION: synthetic

<400> SEQUENCE: 6

| | | | | | |
|---|---|---|---|---|---|
| ttaggtaccg | gcgcactccc | gttctggata | atgttttttg | cgccgacatc | ataacggttc | 60 |
| tggcaaatat | tctgaaatga | gctgttgaca | attaatcatc | gaactagtta | actagtacgc | 120 |
| aagttcacgt | aaaagggtg | atatcatt | | | | 148 |

<210> SEQ ID NO 7
<211> LENGTH: 290
<212> TYPE: DNA
<213> ORGANISM: Artificial Sequence
<220> FEATURE:
<223> OTHER INFORMATION: synthetic

<400> SEQUENCE: 7

| | | | | | |
|---|---|---|---|---|---|
| ttaggtaccg | gcgcactccc | gttctggata | atgttttttg | cgccgacatc | ataacggttc | 60 |
| tggcaaatat | tctgaatgag | ctgttgacaa | ttaatcatcg | aactagttaa | ctagtacgca | 120 |
| agttcacgta | aaagggtat | cgacaatgaa | agcaattttc | gtactgaaag | gttggtggcg | 180 |
| cacttcctga | aacgggcagt | gtattcacca | tgcgtaaagc | aatcagatac | ccagcccgcc | 240 |
| taatgagcgg | gcttttttt | gaacaaaatt | agagaataac | agatatcatt | | 290 |

<210> SEQ ID NO 8
<211> LENGTH: 5025
<212> TYPE: DNA
<213> ORGANISM: Artificial Sequence
<220> FEATURE:
<223> OTHER INFORMATION: synthetic

<400> SEQUENCE: 8

| | | | | | |
|---|---|---|---|---|---|
| aagcttttcg | atcccttatt | tgtagagctc | atccatgcca | tgtgtaatcc | cagcagcagt | 60 |
| tacaaactca | agaaggacca | tgtggtcacg | cttttcgttg | ggatctttcg | aaagggcaga | 120 |
| ttgtgtcgac | aggtaatggt | tgtctggtaa | aaggacaggg | ccatcgccaa | ttggagtatt | 180 |
| ttgttgataa | tggtctgcta | gttgaacgga | tccatcttca | atgttgtggc | gaattttgaa | 240 |
| gttagctttg | attccattct | tttgtttgtc | tgccgtgatg | tatacattgt | gtgagttata | 300 |
| gttgtactcg | agtttgtgtc | cgagaatgtt | tccatcttct | ttaaaatcaa | taccttttaa | 360 |
| ctcgatacga | ttaacaaggg | tatcaccttc | aaacttgact | tcagcacgcg | tcttgtagtt | 420 |
| cccgtcatct | ttgaaagata | tagtgcgttc | ctgtacataa | ccttcgggca | tggcactctt | 480 |
| gaaaaagtca | tgccgtttca | tatgatccgg | ataacgggaa | aagcattgaa | caccataaga | 540 |
| gaaagtagtg | acaagtgttg | gccatggaac | aggtagtttt | ccagtagtgc | aaataaattt | 600 |

```
aagggtaagt tttccgtatg ttgcatcacc ttcaccctct ccactgacag aaaatttgtg    660
cccattaaca tcaccatcta attcaacaag aattgggaca actccagtga aaagttcttc    720
tcctttactc atgatatcgg gtaccgagct cgaattcact ggccgtcgtt ttacaacgtc    780
gtgactggga aaaccctggc gttacccaac ttaatcgcct tgcagcacat ccccctttcg    840
ccagctggcg taatagcgaa gaggcccgca ccgatcgccc ttcccaacag ttgcgcagcc    900
tgaatggcga atgcgcctg atgcggtatt ttctccttac gcatctgtgc ggtatttcac     960
accgcatatg gtgcactctc agtacaatct gctctgatgc cgcatagtta agccagcccc   1020
gacacccgcc aacacccgct gacgagctta gtaaagccct cgctagattt taatgcggat   1080
gttgcgatta cttcgccaac tattgcgata caagaaaaa gccagccttt catgatatat    1140
ctcccaattt gtgtagggct tattatgcac gcttaaaaat aataaaagca gacttgacct   1200
gatagtttgg ctgtgagcaa ttatgtgctt agtgcatcta acgcttgagt taagccgcgc   1260
cgcgaagcgg cgtcggcttg aacgaattgt tagacattat ttgccgacta ccttggtgat   1320
ctcgcctttc acgtagtgga caaattcttc caactgatct gcgcgcgagg ccaagcgatc   1380
ttcttcttgt ccaagataag cctgtctagc ttcaagtatg acgggctgat actgggccgg   1440
caggcgctcc attgcccagt cggcagcgac atccttcggc gcgattttgc cggttactgc   1500
gctgtaccaa atgcgggaca acgtaagcac tacatttcgc tcatcgccag cccagtcggg   1560
cggcgagttc catagcgtta aggtttcatt tagcgcctca aatagatcct gttcaggaac   1620
cggatcaaag agttcctccg ccgctggacc taccaaggca acgctatgtt ctcttgcttt   1680
tgtcagcaag atagccagat caatgtcgat cgtggctggc tcgaagatac ctgcaagaat   1740
gtcattgcgc tgccattctc caaattgcag ttcgcgctta gctggataac gccacggaat   1800
gatgtcgtcg tgcacaacaa tggtgacttc tacagcgcgg agaatctcgc tctctccagg   1860
ggaagccgaa gtttccaaaa ggtcgttgat caaagctcgc cgcgttgttt catcaagcct   1920
tacggtcacc gtaaccagca aatcaatatc actgtgtggc ttcaggccgc catccactgc   1980
ggagccgtac aaatgtacgg ccagcaacgt cggttcgaga tggcgctcga tgacgccaac   2040
tacctctgat agttgagtcg atacttcggc gatcaccgct tccctcatga tgtttaactt   2100
tgttttaggg cgactgccct gctgcgtaac atcgttgctg ctccataaca tcaaacatcg   2160
acccacggcg taacgcgctt gctgcttgga tgcccgaggc atagactgta ccccaaaaaa   2220
acagtcataa caagccatga aaaccgccac tgcgccgtta ccaccgctgc gttcggtcaa   2280
ggttctggac cagttgcgtg agcgcatacg ctacttgcat tacagcttac gaaccgaaca   2340
ggcttatgtc cactgggttc gtgccttcat ccgtttccac ggtgtgcgtc acccggcaac   2400
cttgggcagc agcgaagtcg aggcatttct gtcctggctg gcgaacgagc gcaaggtttc   2460
ggtctccacg catcgtcagg cattggcggc cttgctgttc ttctacggca aggtgctgtg   2520
cacggatctg ccctggcttc aggagatcgg aagacctcgg ccgtcgcggc gcttgccggt   2580
ggtgctgacc ccggatgaag tggttcgcat cctcggtttt ctggaaggcg agcatcgttt   2640
gttcgcccag cttctgtatg gaacgggcat gcggatcagt gagggtttgc aactgcgggt   2700
caaggatctg gatttcgatc acggcacgat catcgtgcgg gagggcaagg gctccaagga   2760
tcgggccttg atgttacccg agagcttggc acccagcctg cgcgagcagg ggaattaatt   2820
cccacgggtt ttgctgcccg caaacgggct gttctggtgt tgctagtttg ttatcagaat   2880
cgcagatccg gcttcagccg gtttgccggc tgaaagcgct atttcttcca gaattgccat   2940
```

```
gattttttcc ccacgggagg cgtcactggc tcccgtgttg tcggcagctt tgattcgata    3000
agcagcatcg cctgtttcag gctgtctatg tgtgactgtt gagctgtaac aagttgtctc    3060
aggtgttcaa tttcatgttc tagttgcttt gttttactgg tttcacctgt tctattaggt    3120
gttacatgct gttcatctgt tacattgtcg atctgttcat ggtgaacagc tttgaatgca    3180
ccaaaaactc gtaaaagctc tgatgtatct atctttttta caccgttttc atctgtgcat    3240
atggacagtt ttccctttga tatgtaacgg tgaacagttg ttctactttt gtttgttagt    3300
cttgatgctt cactgataga tacaagagcc ataagaacct cagatccttc cgtatttagc    3360
cagtatgttc tctagtgtgg ttcgttgttt ttgcgtgagc catgagaacg aaccattgag    3420
atcatactta ctttgcatgt cactcaaaaa ttttgcctca aaactggtga gctgaatttt    3480
tgcagttaaa gcatcgtgta gtgttttttct tagtccgtta tgtaggtagg aatctgatgt    3540
aatggttgtt ggtattttgt caccattcat ttttatctgg ttgttctcaa gttcggttac    3600
gagatccatt tgtctatcta gttcaacttg gaaaatcaac gtatcagtcg ggcggcctcg    3660
cttatcaacc accaatttca tattgctgta agtgtttaaa tctttactta ttggtttcaa    3720
aacccattgg ttaagccttt taaactcatg gtagttattt tcaagcatta acatgaactt    3780
aaattcatca aggctaatct ctatatttgc cttgtgagtt ttcttttgtg ttagttcttt    3840
taataaccac tcataaatcc tcatagagta tttgttttca aaagacttaa catgttccag    3900
attatatttt tgaatttttt ttaactggaa aagataaggc aatatctctt cactaaaaac    3960
taattctaat ttttcgcttg agaacttggc atagtttgtc cactggaaaa tctcaaagcc    4020
tttaaccaaa ggattcctga tttccacagt tctcgtcatc agctctctgg ttgctttagc    4080
taatacacca taagcatttt ccctactgat gttcatcatc tgagcgtatt ggttataagt    4140
gaacgatacc gtccgttctt tccttgtagg ttttcaatc gtggggttga gtagtgccac    4200
acagcataaa attagcttgg tttcatgctc cgttaagtca tagcgactaa tcgctagttc    4260
atttgctttg aaaacaacta attcagacat acatctcaat tggtctaggt gattttaatc    4320
actataccaa ttgagatggg ctagtcaatg ataattacta gtccttttcc tttgagttgt    4380
gggtatctgt aaattctgct agaccttttgc tggaaaactt gtaaattctg ctagaccctc    4440
tgtaaattcc gctagacctt tgtgtgtttt ttttgtttat attcaagtgg ttataattta    4500
tagaataaag aaagaataaa aaagataaa aagaatagat cccagccctg tgtataactc    4560
actactttag tcagttccgc agtattacaa aaggatgtcg caaacgctgt tgctcctct    4620 acaaaacaga ccttaaaacc ctaaaggctt aagtagcacc ctcgcaagct cgggcaaatc    4680
gctgaatatt ccttttgtct ccgaccatca ggcacctgag tcgctgtctt tttcgtgaca    4740
ttcagttcgc tgcgctcacg gctctggcag tgaatggggg taaatggcac tacaggcgcc    4800
ttttatggat tcatgcaagg aaactaccca taatacaaga aaagcccgtc acgggcttct    4860
cagggcgttt tatggcgggt ctgctatgtg gtgctatctg acttttttgct gttcagcagt    4920 tcctgccctc tgattttcca gtctgaccac ttccggattat cccgtgacag gtcattcaga    4980
ctggctaatg cacccagtaa ggcagcggta tcatcaacag gctta               5025

<210> SEQ ID NO 9
<211> LENGTH: 6564
<212> TYPE: DNA
<213> ORGANISM: Escherichia coli

<400> SEQUENCE: 9
cccgatatca tgcaaacaca aaaaccgact ctcgaactgc taacctgcga aggcgcttat    60
```

```
cgcgacaatt ccaccgcgct ttttcaccag ttgtgtgggg atcgtccggc aacgctgctg    120
ctggaatccg cagatatcga cagcaaagat gatttaaaaa gcctgctgct ggtagacagt    180
gcgctgcgca ttacagcttt aggtgacact gtcacaatcc aggcactttc cggcaacggc    240
gaagccctcc tggcactact ggataacgcc ctgcctgcgg gtgtggaaag tgaacaatca    300
ccaaactgcc gtgtgctgcg cttccccccct gtcagtccac tgctggatga agacgcccgc    360
ttatgctccc tttcggtttt tgacgctttc cgtttattgc agaatctgtt gaatgtaccg    420
aaggaagaac gagaagccat gttcttcggc ggcctgttct cttatgacct tgtggcggga    480
tttgaagatt taccgcaact gtcagcggaa ataactgcc ctgatttctg tttttatctc    540
gctgaaacgc tgatggtgat tgaccatcag aaaaaaagca cccgtattca ggccagcctg    600
tttgctccga atgaagaaga aaacaacgt ctcactgctc gcctgaacga actacgtcag    660
caactgaccg aagccgcgcc gccgctgcca gtggtttccg tgccgcatat gcgttgtgaa    720
tgtaatcaga gcgatgaaga gttcggtggc gtagtgcgtt tgttgcaaaa agcgattcgc    780
gctggagaaa ttttccaggt ggtgccatct cgccgtttct ctctgccctg cccgtcaccg    840
ctggcggcct attacgtgct gaaaaagagt aatcccagcc cgtacatgtt ttttatgcag    900
gataatgatt tcaccctatt tggcgcgtcg ccggaaagct cgctcaagta tgatgccacc    960
agccgccaga ttgagatcta cccgattgcc ggaacacgcc cacgcggtcg tcgcgccgat   1020
ggttcactgg acagagatct cgacagccgt attgaactgg aaatgcgtac cgatcataaa   1080
gagctgtctg aacatctgat gctggttgat ctcgcccgta atgatctggc acgcatttgc   1140
acccccggca gccgctacgt cgccgatctc accaaagttg accgttattc ctatgtgatg   1200
cacctcgtct ctcgcgtagt cggcgaactg cgtcacgatc ttgacgccct gcacgcttat   1260
cgcgcctgta tgaatatggg gacgttaagc ggtgcgccga agtacgcgc tatgcagtta    1320 attgccgagg cggaaggtcg tcgccgcggc agctacggcg gcgcgtagg ttatttcacc    1380 gcgcatggcg atctcgacac ctgcattgtg atccgctcgg cgctggtgga aaacggtatc   1440
gccaccgtgc aagcgggtgc tggtgtagtc cttgattctg ttccgcagtc ggaagccgac   1500
gaaacccgta caaagcccg cgctgtactg cgcgctattg ccaccgcgca tcatgcacag   1560
gagactttct gatggctgac attctgctgc tcgataatat cgactctttt acgtacaacc   1620
tggcagatca gttgcgcagc aatgggcata acgtggtgat ttaccgcaac catattccgg   1680
cgcaaacctt aattgaacgc ctggcgacca tgagcaatcc ggtgctgatg ctttctcctg   1740
gccccggtgt gccgagcgaa gccggttgta tgccggaact cctcacccgc ttgcgtggca   1800
agctgcccat tattggcatt tgcctcggac atcaggcgat tgtcgaagct tacggggct    1860 atgtcggtca ggcgggcgaa attctccacg gtaaagcctc cagcattgaa catgacggtc   1920
aggcgatgtt tgccggatta acaaacccgc tgccggtggc gcgttatcac tcgctggttg   1980
gcagtaacat tccggccggt ttaaccatca acgcccattt taatggcatg gtgatggcag   2040
tacgtcacga tgcggatcgc gtttgtggat tccagttcca tccggaatcc attctcacca   2100
cccagggcgc tcgcctgctg gaacaaacgc tggcctgggc gcagcagaaa ctagagccag   2160
ccaacacgct gcaaccgatt ctggaaaaac tgtatcaggc agacgcttt agccaacaag   2220 aaagccacca gctgttttca gcggtggtgc gtggcgagct gaagccggaa caactggcgg   2280
cggcgctggt gagcatgaaa attcgcggtg agcaccgaa cgagatcgcc ggggcagcaa    2340
ccgcgctact ggaaaacgca gcgccgttcc cgcgcccgga ttatctgttt gctgatatcg   2400
```

```
tcggtactgg cggtgacggc agcaacagta tcaatatttc taccgccagt gcgtttgtcg    2460
ccgcggcctg tgggctgaaa gtggcgaaac acggcaaccg tagcgtctcc agtaaatctg    2520
gttcgtccga tctgctggcg gcgttcggta ttaatcttga tatgaacgcc gataaatcgc    2580
gccaggcgct ggatgagtta ggtgtatgtt cctctttttgc gccgaagtat cacaccggat   2640
tccgccacgc gatgccggtt cgccagcaac tgaaaacccg caccctgttc aatgtgctgg    2700
ggccattgat taacccggcg catccgccgc tggcgttaat tggtgtttat agtccggaac    2760
tggtgctgcc gattgccgaa accttgcgcg tgctggggta tcaacgcgcg gcggtggtgc    2820
acagcggcgg gatggatgaa gtttcattac acgcgccgac aatcgttgcc gaactgcatg    2880
acggcgaaat taaaagctat cagctcaccg cagaagactt tggcctgaca ccctaccacc    2940
aggagcaact ggcaggcgga acaccggaag aaaaccgtga cattttaaca cgtttgttac    3000
aaggtaaagg cgacgccgcc catgaagcag ccgtcgctgc gaacgtcgcc atgttaatgc    3060
gcctgcatgg ccatgaagat ctgcaagcca atgcgcaaac cgttcttgag gtactgcgca    3120
gtggttccgc ttacgacaga gtcaccgcac tggcggcacg agggtaaatg atgcaaaccg    3180
ttttagcgaa aatcgtcgca gacaaggcga tttgggtaga agcccgcaaa cagcagcaac    3240
cgctggccag ttttcagaat gaggttcagc cgagcacgcg acattttat gatgcgctac     3300
agggtgcgcg cacggcgttt attctggagt gcaagaaagc gtcgccgtca aaaggcgtga    3360
tccgtgatga tttcgatcca gcacgcattg ccgccattta taaacattac gcttcggcaa    3420
tttcggtgct gactgatgag aaatatttc aggggagctt taatttcctc cccatcgtca     3480
gccaaatcgc cccgcagccg attttatgta aagacttcat tatcgaccct taccagatct    3540
atctggcgcg ctattaccag gccgatgcct gcttattaat gctttcagta ctggatgacg    3600
accaatatcg ccagcttgcc gccgtcgctc acagtctgga gatgggggtg ctgaccgaag    3660
tcagtaatga agaggaacag gagcgcgcca ttgcattggg agcaaaggtc gttggcatca    3720
acaaccgcga tctgcgtgat tgtcgattga tctcaaccg tacccgcgag cttgcgccga    3780
aactgggggca caacgtgacg gtaatcagcg aatccggcat caatacttac gctcaggtgc    3840
gcgagttaag ccacttcgct aacgttttc tgattggttc ggcgttgatg gcccatgacg     3900
atttgcacgc cgccgtgcgc cgggtgttgc tgggtgagaa taaagtatgt ggcctgacgc    3960
gtgggcaaga tgctaaagca gcttatgacg cgggcgcgat ttacggtggg ttgattttg     4020
ttgcgacatc accgcgttgc gtcaacgttg aacaggcgca ggaagtgatg gctgcggcac    4080
cgttgcagta tgttggcgtg ttccgcaatc acgatattgc cgatgtggtg gacaaagcta    4140
aggtgttatc gctggcggca gtgcaactgc atggtaatga agaacagctg tatatcgata    4200
cgctgcgtga agctctgcca gcacatgttg ccatctggaa agcattaagc gtcggtgaaa    4260
ccctgcccgc ccgcgagttt cagcacgttg ataaatatgt tttagacaac ggccagggtg    4320
gaagcgggca acgttttgac tggtcactat taaatggtca atcgcttggc aacgttctgc    4380
tggcgggggg cttaggcgca gataactgcg tggaagcggc acaaaccggc tgcgccggac    4440
ttgattttaa ttctgctgta gagtcgcaac cgggcatcaa agacgcacgt ctttttggcct    4500
cggttttcca gacgctgcgc gcatattaag gaaaggaaca atgacaacat tacttaaccc    4560
ctattttggt gagtttggcg catgtacgt gccacaaatc ctgatgcctg ctctgcgcca     4620
gctggaagaa gcttttgtca gtgcgcaaaa agatcctgaa tttcaggctc agttcaacga    4680
cctgctgaaa aactatgccg ggcgtccaac cgcgctgacc aaatgccaga acattacagc    4740
cgggacgaac accacgctgt atctcaagcg tgaagatttg ctgcacggcg gcgcgcataa    4800
```

```
aactaaccag gtgctggggc aggcgttgct ggcgaagcgg atgggtaaaa ccgaaatcat    4860
cgccgaaacc ggtgccggtc agcatggcgt ggcgtcggcc cttgccagcg ccctgctcgg    4920
cctgaaatgc cgtatttata tgggtgccaa agacgttgaa cgccagtcgc ctaacgtttt    4980
tcgtatgcgc ttaatgggtg cggaagtgat cccggtgcat agcggttccg cgacgctgaa    5040
agatgcctgt aacgaggcgc tgcgcgactg gtccggtagt tacgaaaccg cgcactatat    5100
gctgggcacc gcagctggcc cgcatcctta tccgaccatt gtgcgtgagt ttcagcggat    5160
gattggcgaa gaaaccaaag cgcagattct ggaaagagaa ggtcgcctgc cggatgccgt    5220
tatcgcctgt gttggcggcg gttcgaatgc catcggcatg tttgctgatt tcatcaatga    5280
aaccaacgtc ggcctgattg tgtggagcc aggtggtcac ggtatcgaaa ctggcgagca    5340
cggcgcaccg ctaaaacatg gtcgcgtggg tatctatttc ggtatgaaag cgccgatgat    5400
gcaaaccgaa gacgggcaga ttgaagaatc ttactccatc tccgccggac tggatttccc    5460
gtctgtcggc ccacaacacg cgtatcttaa cagcactgga cgcgctgatt acgtgtctat    5520
taccgatgat gaagcccttg aagccttcaa aacgctgtgc ctgcacgaag ggatcatccc    5580
ggcgctggaa tcctcccacg ccctggccca tgcgttgaaa atgatgcgcg aaaacccgga    5640
taaagagcag ctactggtgg ttaaccttt cggtcgcggc gataaagaca tcttcaccgt    5700
tcacgatatt ttgaaagcac gaggggaaat ctgatggaac gctacgaatc tctgtttgcc    5760
cagttgaagg agcgcaaaga aggcgcattc gttccttttcg tcacgctcgg tgatccgggc    5820
attgagcagt cattgaaaat tatcgatacg ctaattgaag ccggtgctga cgcgctggag    5880
ttaggtatcc ccttctccga cccactggcg gatggcccga cgattcaaaa cgccactctg    5940
cgcgcctttg cggcaggtgt gactccggca caatgttttg aaatgctggc actgattcgc    6000
cagaaacacc cgaccattcc cattggcctg ttgatgtatg ccaatctggt gtttaacaaa    6060
ggcattgatg agttttatgc ccagtgcgaa aaagtcggcg tcgattcggt gctggttgcc    6120
gatgtgccag ttgaagagtc cgcgcccttc cgccaggccg cgttgcgtca taatgtcgca    6180
cctatcttca tctgcccgcc aaatgccgat gacgacctgc tgcgccagat agcctcttac    6240
ggtcgtggtt acacctattt gctgtcacga gcaggcgtga ccggcgcaga aaaccgcgcc    6300
gcgttacccc tcaatcatct ggttgcgaag ctgaaagagt acaacgctgc acctccattg    6360
cagggatttg gtatttccgc cccggatcag gtaaaagcag cgattgatgc aggagctgcg    6420
ggcgcgattt ctggttcggc cattgttaaa atcatcgagc aacatattaa tgagccagag    6480
aaaatgctgg cggcactgaa agttttttgta caaccgatga agcggcgac gcgcagttaa    6540 tcccacggat cctttaagct tccc                                          6564
```

<210> SEQ ID NO 10
<211> LENGTH: 5002
<212> TYPE: DNA
<213> ORGANISM: Escherichia coli

<400> SEQUENCE: 10

```
aaagatatca tggctgacat tctgctgctc gataatatcg actcttttac gtacaacctg      60
gcagatcagt tgcgcagcaa tgggcataac gtggtgattt accgcaacca tattccggcg     120
caaaccttaa ttgaacgcct ggcgaccatg agcaatccgg tgctgatgct ttctcctggc     180
cccggtgtgc cgagcgaagc cggttgtatg ccggaactcc tcacccgctt gcgtggcaag     240
ctgcccatta ttggcatttg cctcggacat caggcgattg tcgaagctta cgggggctat     300
```

```
gtcggtcagg cgggcgaaat tctccacggt aaagcctcca gcattgaaca tgacggtcag    360
gcgatgtttg ccggattaac aaacccgctg ccggtggcgc gttatcactc gctggttggc    420
agtaacattc cggccggttt aaccatcaac gcccatttta atggcatggt gatggcagta    480
cgtcacgatg cggatcgcgt ttgtggattc cagttccatc cggaatccat tctcaccacc    540
cagggcgctc gcctgctgga caaacgctg gcctgggcgc agcagaaact agagccagcc    600
aacacgctgc aaccgattct ggaaaaactg tatcaggcgc agacgcttag ccaacaagaa    660
agccaccagc tgttttcagc ggtggtgcgt ggcgagctga agccggaaca actggcggcg    720
gcgctggtga gcatgaaaat cgcggtgag cacccgaacg agatcgccgg ggcagcaacc    780
gcgctactgg aaaacgcagc gccgttcccg cgcccggatt atctgtttgc tgatatcgtc    840
ggtactggcg gtgacggcag caacagtatc aatatttcta ccgccagtgc gtttgtcgcc    900
gcggcctgtg gctgaaagt ggcgaaacac ggcaaccgta gcgtctccag taaatctggt    960
tcgtccgatc tgctggcggc gttcggtatt aatcttgata tgaacgccga taaatcgcgc   1020
caggcgctgg atgagttagg tgtatgtttc ctctttgcgc cgaagtatca caccggattc   1080
cgccacgcga tgccggttcg ccagcaactg aaaacccgca ccctgttcaa tgtgctgggg   1140
ccattgatta acccggcgca tccgccgctg gcgttaattg gtgtttatag tccggaactg   1200
gtgctgccga ttgccgaaac cttgcgcgtg ctggggtatc aacgcgcggc ggtggtgcac   1260
agcggcggga tggatgaagt ttcattacac gcgccgacaa tcgttgccga actgcatgac   1320
ggcgaaatta aagctatca gctcaccgca gaagactttg gcctgacacc ctaccaccag   1380
gagcaactgg caggcggaac accggaagaa aaccgtgaca ttttaacacg tttgttacaa   1440
ggtaaaggcg acgccgccca tgaagcagcc gtcgctgcga acgtcgccat gttaatgcgc   1500
ctgcatggcc atgaagatct gcaagccaat gcgcaaaccg ttcttgaggt actgcgcagt   1560
ggttccgctt acgacagagt caccgcactg gcggcacgag ggtaaatgat gcaaaccgtt   1620
ttagcgaaaa tcgtcgcaga caaggcgatt tgggtagaag cccgcaaaca gcagcaaccg   1680
ctggccagtt ttcagaatga ggttcagccg agcacgcgac attttatga tgcgctacag   1740 ggtgcgcgca cggcgtttat tctggagtgc aagaaagcgt cgccgtcaaa aggcgtgatc   1800
cgtgatgatt tcgatccagc acgcattgcc gccatttata acattacgc ttcggcaatt   1860 tcggtgctga ctgatgagaa atattttcag gggagcttta atttcctccc catcgtcagc   1920
caaatcgccc cgcagccgat tttatgtaaa gacttcatta tcgacccta ccagatctat   1980 ctggcgcgct attaccaggc cgatgcctgc ttattaatgc tttcagtact ggatgacgac   2040
caatatcgcc agcttgccgc cgtcgctcac agtctggaga tgggggtgct gaccgaagtc   2100
agtaatgaag aggaacagga gcgcgccatt gcattgggag caaaggtcgt tggcatcaac   2160
aaccgcgatc tgcgtgattt gtcgattgat ctcaaccgta cccgcgagct tgcgccgaaa   2220
ctggggcaca acgtgacggt aatcagcgaa tccggcatca atacttacgc tcaggtgcgc   2280
gagttaagcc acttcgctaa cggttttctg attggttcgg cgttgatggc ccatgacgat   2340
ttgcacgccg ccgtgcgccg ggtgttgctg ggtgagaata agtatgtgg cctgacgcgt   2400 gggcaagatg ctaaagcagc ttatgacgcg ggcgcgattt acggtgggtt gattttttgtt   2460 gcgacatcac cgcgttgcgt caacgttgaa caggcgcagg aagtgatggc tgcggcaccg   2520
ttgcagtatg ttggcgtgtt ccgcaatcac gatattgccg atgtggtgga caaagctaag   2580
gtgttatcgc tggcggcagt gcaactgcat ggtaatgaag aacagctgta tatcgatacg   2640
ctgcgtgaag ctctgccagc acatgttgcc atctggaaag cattaagcgt cggtgaaacc   2700
```

```
ctgcccgccc gcgagtttca gcacgttgat aaatatgttt tagacaacgg ccagggtgga    2760
agcgggcaac gttttgactg gtcactatta aatggtcaat cgcttggcaa cgttctgctg    2820 gcgggggget taggcgcaga taactgcgtg gaagcggcac aaaccggctg cgccggactt    2880
gattttaatt ctgctgtaga gtcgcaaccg ggcatcaaag acgcacgtct tttggcctcg    2940
gttttccaga cgctgcgcgc atattaagga aaggaacaat gacaacatta cttaacccct    3000
attttggtga gttggcggc atgtacgtgc cacaaatcct gatgcctgct ctgcgccagc     3060
tggaagaagc ttttgtcagt gcgcaaaaag atcctgaatt tcaggctcag ttcaacgacc    3120
tgctgaaaaa ctatgccggg cgtccaaccg cgctgaccaa atgccagaac attacagccg    3180
ggacgaacac cacgctgtat ctcaagcgtg aagatttgct gcacggcggc gcgcataaaa   3240
ctaaccaggt gctggggcag gcgttgctgg cgaagcggat gggtaaaacc gaaatcatcg    3300
ccgaaaccgg tgccggtcag catggcgtgg cgtcggccct tgccagcgcc ctgctcggcc    3360
tgaaatgccg tatttatatg ggtgccaaag acgttgaacg ccagtcgcct aacgtttttc    3420
gtatgcgctt aatgggtgcg gaagtgatcc cggtgcatag cggttccgcg acgctgaaag    3480
atgcctgtaa cgaggcgctg cgcgactggt ccggtagtta cgaaaccgcg cactatatgc    3540
tgggcaccgc agctggcccg catccttatc cgaccattgt gcgtgagttt cagcggatga    3600
ttggcgaaga aaccaaagcg cagattctgg aaagagaagg tcgcctgccg gatgccgtta    3660
tcgcctgtgt tggcggcggt tcgaatgcca tcggcatgtt tgctgatttc atcaatgaaa    3720
ccaacgtcgg cctgattggt gtggagccag gtggtcacgg tatcgaaact ggcgagcacg    3780
gcgcaccgct aaaacatggt cgcgtgggta tctatttcgg tatgaaagcg ccgatgatgc    3840
aaaccgaaga cgggcagatt gaagaatctt actccatctc cgccgactg gatttcccgt     3900 ctgtcggccc acaacacgcg tatcttaaca gcactggacg cgctgattac gtgtctatta    3960
ccgatgatga agcccttgaa gccttcaaaa cgctgtgcct gcacgaaggg atcatcccgg    4020
cgctggaatc ctcccacgcc ctggcccatg cgttgaaaat gatgcgcgaa aacccggata    4080
aagagcagct actggtggtt aacctttccg gtcgcggcga taaagacatc ttcaccgttc    4140
acgatatttt gaaagcacga ggggaaatct gatggaacgc tacgaatctc tgtttgccca    4200
gttgaaggag cgcaaagaag gcgcattcgt tcctttcgtc acgctcggtg atccgggcat    4260
tgagcagtca ttgaaaatta tcgatacgct aattgaagcc ggtgctgacg cgctggagtt    4320 aggtatccc ttctccgacc cactggcgga tgggccgacg attcaaaacg ccactctgcg     4380
cgcctttgcg gcaggtgtga ctccggcaca atgttttgaa atgctggcac tgattcgcca    4440
gaaacacccg accattccca ttggcctgtt gatgtatgcc aatctggtgt taacaaagg    4500 cattgatgag ttttatgccc agtgcgaaaa agtcggcgtc gattcggtgc tggttgccga    4560
tgtgccagtt gaagagtccg cgcccttccg ccaggccgcg ttgcgtcata atgtcgcacc    4620
tatcttcatc tgcccgccaa atgccgatga cgacctgctg cgccagatag cctcttacgg    4680
tcgtggttac acctatttgc tgtcacgagc aggcgtgacc ggcgcagaaa accgcgccgc    4740
gttacccctc aatcatctgg ttgcgaagct gaaagagtac aacgctgcac ctccattgca    4800
gggatttggt atttccgccc cggatcaggt aaaagcagcg attgatgcag agctgcgggg    4860
cgcgatttct ggttcggcca ttgttaaaat catcgagcaa catattaatg agccagagaa    4920
aatgctggcg gcactgaaag ttttgtgtaca accgatgaaa gcggcgacgc gcagttaatc    4980
ccacggatcc tttaagcttc cc                                             5002
```

```
<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
ttaggtaccg gcgcactccc gttctggata                                    30

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
actgcccgtt gtcgataccc tttttacgt                                     29

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
tcgacaacgg gcagtgtatt caccatg                                       27

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
aatgatatct gttattctct aattttgtt                                     29

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
aatgatatca ccctttttac gtgaacttg                                     29

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
cccgatatca tgcaaacaca aaaaccgac                                     29

<210> SEQ ID NO 17
<211> LENGTH: 45
<212> TYPE: DNA
<213> ORGANISM: Artificial Sequence
<220> FEATURE:
<223> OTHER INFORMATION: primer
```

<400> SEQUENCE: 17
gggaagctta aaggatccgt gggattaact gcgcgtcgcc gcttt                    45

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
aaagatatca tggctgacat tctgctgct                                      29

<210> SEQ ID NO 19
<211> LENGTH: 70
<212> TYPE: DNA
<213> ORGANISM: Artificial Sequence
<220> FEATURE:
<223> OTHER INFORMATION: primer

<400> SEQUENCE: 19
ggcctcccaa atcgggggc cttttttatt gataacaaaa aggcaacact aggtgacact     60
atagaacgcg                                                           70

<210> SEQ ID NO 20
<211> LENGTH: 70
<212> TYPE: DNA
<213> ORGANISM: Artificial Sequence
<220> FEATURE:
<223> OTHER INFORMATION: primer

<400> SEQUENCE: 20
aacagcccaa taccttcatt gaacgggtga tttcccctaa ctctttcaat tagtggatct    60
gatgggtacc                                                           70

<210> SEQ ID NO 21
<211> LENGTH: 70
<212> TYPE: DNA
<213> ORGANISM: Artificial Sequence
<220> FEATURE:
<223> OTHER INFORMATION: primer

<400> SEQUENCE: 21
gaatgggagg cgtttcgtcg tgtgaaacag aatgcgaaga cgaacaataa ggcctcccaa    60
atcgggggc                                                            70

<210> SEQ ID NO 22
<211> LENGTH: 70
<212> TYPE: DNA
<213> ORGANISM: Artificial Sequence
<220> FEATURE:
<223> OTHER INFORMATION: primer

<400> SEQUENCE: 22 ggcaccttt catcaggttg gatcaacagg cactacgttc tcacttgggt aacagcccaa     60
taccttcatt                                                           70

<210> SEQ ID NO 23
<211> LENGTH: 20
<212> TYPE: DNA
<213> ORGANISM: Artificial Sequence
<220> FEATURE:

<223> OTHER INFORMATION: primer

<400> SEQUENCE: 23
ttgagtgtat cgccaacgcg                                                   20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
aaagccgcgt gttattgcgt                                                   20

<210> SEQ ID NO 25
<211> LENGTH: 70
<212> TYPE: DNA
<213> ORGANISM: Artificial Sequence
<220> FEATURE:
<223> OTHER INFORMATION: primer

<400> SEQUENCE: 25
ttagccaaat ttaggtaaca cgttaaagac gttgccgaac cagcacaaaa aggtgacact       60
atagaacgcg                                                              70

<210> SEQ ID NO 26
<211> LENGTH: 70
<212> TYPE: DNA
<213> ORGANISM: Artificial Sequence
<220> FEATURE:
<223> OTHER INFORMATION: primer

<400> SEQUENCE: 26
atgaaggatt atgtaatgga aaactttaaa catctccctg aaccgttccg tagtggatct       60
gatgggtacc                                                              70

<210> SEQ ID NO 27
<211> LENGTH: 70
<212> TYPE: DNA
<213> ORGANISM: Artificial Sequence
<220> FEATURE:
<223> OTHER INFORMATION: primer

<400> SEQUENCE: 27
tgatttcctg agaggcaaga agccagcgaa tggctggctt cttgaaggat ttagccaaat       60
ttaggtaaca                                                              70

<210> SEQ ID NO 28
<211> LENGTH: 70
<212> TYPE: DNA
<213> ORGANISM: Artificial Sequence
<220> FEATURE:
<223> OTHER INFORMATION: primer

<400> SEQUENCE: 28
aatcggtata gcagatgtaa tattcacagg gatcactgta attaaaataa atgaaggatt       60
atgtaatgga                                                              70

<210> SEQ ID NO 29
<211> LENGTH: 20
<212> TYPE: DNA
<213> ORGANISM: Artificial Sequence

```
<220> FEATURE:
<223> OTHER INFORMATION: primer

<400> SEQUENCE: 29
cgggataaag taaaaccagg                                              20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cggcgaaggt aagttgatga                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tatttgctgt cacgagcagg                                              20

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
agttccggca tacaaccggc tt                                           22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
taatacgact cactataggg                                              20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ctgttgggcg gaaaaatgac                                              20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tgatcgccag ggtgccgacg                                              20
```

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ccctatagtg agtcgtatta                                                   20

<210> SEQ ID NO 37
<211> LENGTH: 531
<212> TYPE: PRT
<213> ORGANISM: Escherichia coli

<400> SEQUENCE: 37

Met Ala Asp Ile Leu Leu Asp Asn Ile Asp Ser Phe Thr Tyr Asn
1               5                   10                  15

Leu Ala Asp Gln Leu Arg Ser Asn Gly His Asn Val Val Ile Tyr Arg
                20                  25                  30

Asn His Ile Pro Ala Gln Thr Leu Ile Glu Arg Leu Ala Thr Met Ser
            35                  40                  45

Asn Pro Val Leu Met Leu Ser Pro Gly Pro Gly Val Pro Ser Glu Ala
        50                  55                  60

Gly Cys Met Pro Glu Leu Leu Thr Arg Leu Arg Gly Lys Leu Pro Ile
65                  70                  75                  80

Ile Gly Ile Cys Leu Gly His Gln Ala Ile Val Glu Ala Tyr Gly Gly
                85                  90                  95

Tyr Val Gly Gln Ala Gly Glu Ile Leu His Gly Lys Ala Ser Ser Ile
                100                 105                 110

Glu His Asp Gly Gln Ala Met Phe Ala Gly Leu Thr Asn Pro Leu Pro
            115                 120                 125

Val Ala Arg Tyr His Ser Leu Val Gly Ser Asn Ile Pro Ala Gly Leu
        130                 135                 140

Thr Ile Asn Ala His Phe Asn Gly Met Val Met Ala Val Arg His Asp
145                 150                 155                 160

Ala Asp Arg Val Cys Gly Phe Gln Phe His Pro Glu Ser Ile Leu Thr
                165                 170                 175

Thr Gln Gly Ala Arg Leu Leu Glu Gln Thr Leu Ala Trp Ala Gln Gln
            180                 185                 190

Lys Leu Glu Pro Ala Asn Thr Leu Gln Pro Ile Leu Glu Lys Leu Tyr
        195                 200                 205

Gln Ala Gln Thr Leu Ser Gln Gln Glu Ser His Gln Leu Phe Ser Ala
    210                 215                 220

Val Val Arg Gly Glu Leu Lys Pro Glu Gln Leu Ala Ala Ala Leu Val
225                 230                 235                 240

Ser Met Lys Ile Arg Gly Glu His Pro Asn Glu Ile Ala Gly Ala Ala
                245                 250                 255

Thr Ala Leu Leu Glu Asn Ala Ala Pro Phe Pro Arg Pro Asp Tyr Leu
            260                 265                 270

Phe Ala Asp Ile Val Gly Thr Gly Gly Asp Gly Ser Asn Ser Ile Asn
        275                 280                 285

Ile Ser Thr Ala Ser Ala Phe Val Ala Ala Cys Gly Leu Lys Val
    290                 295                 300

Ala Lys His Gly Asn Arg Ser Val Ser Ser Lys Ser Gly Ser Ser Asp
305                 310                 315                 320

```
Leu Leu Ala Ala Phe Gly Ile Asn Leu Asp Met Asn Ala Asp Lys Ser
                325                 330                 335

Arg Gln Ala Leu Asp Glu Leu Gly Val Cys Phe Leu Phe Ala Pro Lys
            340                 345                 350

Tyr His Thr Gly Phe Arg His Ala Met Pro Val Arg Gln Gln Leu Lys
        355                 360                 365

Thr Arg Thr Leu Phe Asn Val Leu Gly Pro Leu Ile Asn Pro Ala His
    370                 375                 380

Pro Pro Leu Ala Leu Ile Gly Val Tyr Ser Pro Glu Leu Val Leu Pro
385                 390                 395                 400

Ile Ala Glu Thr Leu Arg Val Leu Gly Tyr Gln Arg Ala Val Val
            405                 410                 415

His Ser Gly Gly Met Asp Glu Val Ser Leu His Ala Pro Thr Ile Val
            420                 425                 430

Ala Glu Leu His Asp Gly Glu Ile Lys Ser Tyr Gln Leu Thr Ala Glu
            435                 440                 445

Asp Phe Gly Leu Thr Pro Tyr His Gln Glu Gln Leu Ala Gly Gly Thr
    450                 455                 460

Pro Glu Glu Asn Arg Asp Ile Leu Thr Arg Leu Leu Gln Gly Lys Gly
465                 470                 475                 480

Asp Ala Ala His Glu Ala Ala Val Ala Ala Asn Val Ala Met Leu Met
                485                 490                 495

Arg Leu His Gly His Glu Asp Leu Gln Ala Asn Ala Gln Thr Val Leu
            500                 505                 510

Glu Val Leu Arg Ser Gly Ser Ala Tyr Asp Arg Val Thr Ala Leu Ala
            515                 520                 525

Ala Arg Gly
    530

<210> SEQ ID NO 38
<211> LENGTH: 452
<212> TYPE: PRT
<213> ORGANISM: Escherichia coli

<400> SEQUENCE: 38

Met Gln Thr Val Leu Ala Lys Ile Val Ala Asp Lys Ala Ile Trp Val
1               5                   10                  15

Glu Ala Arg Lys Gln Gln Gln Pro Leu Ala Ser Phe Gln Asn Glu Val
            20                  25                  30

Gln Pro Ser Thr Arg His Phe Tyr Asp Ala Leu Gln Gly Ala Arg Thr
        35                  40                  45

Ala Phe Ile Leu Glu Cys Lys Lys Ala Ser Pro Ser Lys Gly Val Ile
    50                  55                  60

Arg Asp Asp Phe Asp Pro Ala Arg Ile Ala Ala Ile Tyr Lys His Tyr
65                  70                  75                  80

Ala Ser Ala Ile Ser Val Leu Thr Asp Glu Lys Tyr Phe Gln Gly Ser
                85                  90                  95

Phe Asn Phe Leu Pro Ile Val Ser Gln Ile Ala Pro Gln Pro Ile Leu
            100                 105                 110

Cys Lys Asp Phe Ile Ile Asp Pro Tyr Gln Ile Tyr Leu Ala Arg Tyr
        115                 120                 125

Tyr Gln Ala Asp Ala Cys Leu Leu Met Leu Ser Val Leu Asp Asp Asp
    130                 135                 140

Gln Tyr Arg Gln Leu Ala Ala Val Ala His Ser Leu Glu Met Gly Val
```

| | | | | | | | 145 | | | | 150 | | | | 155 | | | | 160 |

Leu Thr Glu Val Ser Asn Glu Glu Gln Glu Arg Ala Ile Ala Leu
                165                 170                 175

Gly Ala Lys Val Val Gly Ile Asn Asn Arg Asp Leu Arg Asp Leu Ser
            180                 185                 190

Ile Asp Leu Asn Arg Thr Arg Glu Leu Ala Pro Lys Leu Gly His Asn
        195                 200                 205

Val Thr Val Ile Ser Glu Ser Gly Ile Asn Thr Tyr Ala Gln Val Arg
    210                 215                 220

Glu Leu Ser His Phe Ala Asn Gly Phe Leu Ile Gly Ser Ala Leu Met
225                 230                 235                 240

Ala His Asp Asp Leu His Ala Ala Val Arg Arg Val Leu Leu Gly Glu
                245                 250                 255

Asn Lys Val Cys Gly Leu Thr Arg Gly Gln Asp Ala Lys Ala Ala Tyr
            260                 265                 270

Asp Ala Gly Ala Ile Tyr Gly Gly Leu Ile Phe Val Ala Thr Ser Pro
        275                 280                 285

Arg Cys Val Asn Val Glu Gln Ala Gln Glu Val Met Ala Ala Ala Pro
    290                 295                 300

Leu Gln Tyr Val Gly Val Phe Arg Asn His Asp Ile Ala Asp Val Val
305                 310                 315                 320

Asp Lys Ala Lys Val Leu Ser Leu Ala Ala Val Gln Leu His Gly Asn
                325                 330                 335

Glu Glu Gln Leu Tyr Ile Asp Thr Leu Arg Glu Ala Leu Pro Ala His
            340                 345                 350

Val Ala Ile Trp Lys Ala Leu Ser Val Gly Glu Thr Leu Pro Ala Arg
        355                 360                 365

Glu Phe Gln His Val Asp Lys Tyr Val Leu Asp Asn Gly Gln Gly Gly
    370                 375                 380

Ser Gly Gln Arg Phe Asp Trp Ser Leu Leu Asn Gly Gln Ser Leu Gly
385                 390                 395                 400

Asn Val Leu Leu Ala Gly Gly Leu Gly Ala Asp Asn Cys Val Glu Ala
                405                 410                 415

Ala Gln Thr Gly Cys Ala Gly Leu Asp Phe Asn Ser Ala Val Glu Ser
            420                 425                 430

Gln Pro Gly Ile Lys Asp Ala Arg Leu Leu Ala Ser Val Phe Gln Thr
        435                 440                 445

Leu Arg Ala Tyr
    450

<210> SEQ ID NO 39
<211> LENGTH: 397
<212> TYPE: PRT
<213> ORGANISM: Escherichia coli

<400> SEQUENCE: 39

Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
 65                  70                  75                  80

Leu His Gly Gly Ala His Lys Thr Asn Gln Val Leu Gly Gln Ala Leu
             85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
    210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
        275                 280                 285

Thr Glu Asp Gly Gln Ile Glu Glu Ser Tyr Ser Ile Ser Ala Gly Leu
    290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
        355                 360                 365

Glu Gln Leu Leu Val Val Asn Leu Ser Gly Arg Gly Asp Lys Asp Ile
    370                 375                 380

Phe Thr Val His Asp Ile Leu Lys Ala Arg Gly Glu Ile
385                 390                 395

<210> SEQ ID NO 40
<211> LENGTH: 268
<212> TYPE: PRT
<213> ORGANISM: Escherichia coli

<400> SEQUENCE: 40

Met Glu Arg Tyr Glu Ser Leu Phe Ala Gln Leu Lys Glu Arg Lys Glu
1               5                   10                  15

Gly Ala Phe Val Pro Phe Val Thr Leu Gly Asp Pro Gly Ile Glu Gln
            20                  25                  30

Ser Leu Lys Ile Ile Asp Thr Leu Ile Glu Ala Gly Ala Asp Ala Leu
        35                  40                  45

```
Glu Leu Gly Ile Pro Phe Ser Asp Pro Leu Ala Asp Gly Pro Thr Ile
    50                  55                  60
Gln Asn Ala Thr Leu Arg Ala Phe Ala Ala Gly Val Thr Pro Ala Gln
 65             70                  75                      80
Cys Phe Glu Met Leu Ala Leu Ile Arg Gln Lys His Pro Thr Ile Pro
                85                  90                  95
Ile Gly Leu Leu Met Tyr Ala Asn Leu Val Phe Asn Lys Gly Ile Asp
            100                 105                 110
Glu Phe Tyr Ala Gln Cys Glu Lys Val Gly Val Asp Ser Val Leu Val
            115                 120                 125
Ala Asp Val Pro Val Glu Glu Ser Ala Pro Phe Arg Gln Ala Ala Leu
    130                 135                 140
Arg His Asn Val Ala Pro Ile Phe Ile Cys Pro Pro Asn Ala Asp Asp
145                 150                 155                 160
Asp Leu Leu Arg Gln Ile Ala Ser Tyr Gly Arg Gly Tyr Thr Tyr Leu
                165                 170                 175
Leu Ser Arg Ala Gly Val Thr Gly Ala Glu Asn Arg Ala Ala Leu Pro
            180                 185                 190
Leu Asn His Leu Val Ala Lys Leu Lys Glu Tyr Asn Ala Ala Pro Pro
        195                 200                 205
Leu Gln Gly Phe Gly Ile Ser Ala Pro Asp Gln Val Lys Ala Ala Ile
    210                 215                 220
Asp Ala Gly Ala Ala Gly Ala Ile Ser Gly Ser Ala Ile Val Lys Ile
225                 230                 235                 240
Ile Glu Gln His Ile Asn Glu Pro Glu Lys Met Leu Ala Ala Leu Lys
                245                 250                 255
Val Phe Val Gln Pro Met Lys Ala Ala Thr Arg Ser
            260                 265
```

MICROORGANISM OF THE GENUS *ESCHERICHIA* HAVING ENHANCED L-TRYPTOPHAN PRODUCTIVITY AND A METHOD FOR PRODUCING L-TRYPTOPHAN USING THE SAME

CROSS REFERENCE TO RELATED APPLICATIONS

This application is a National Stage Entry of International Application No. PCT/KR2013/000214 (WO 2013/105800), filed on Jan. 10, 2013, and claims the benefit of Korean Application Nos. 10-2012-0002906, filed on Jan. 10, 2012 and 10-2013-0002913, filed on Jan. 10, 2013, each of which is incorporated herein by reference in its entirety for all purposes as if fully set forth herein.

TECHNICAL FIELD

The present invention relates to a microorganism of the genus *Escherichia* having enhanced L-tryptophan productivity, and a method of producing L-tryptophan using the same.

Incorporated by reference herein in its entirety is the Sequence Listing entitled "sequence Listing.txt", created Jul. 8, 2014, size of 44 kilobytes.

BACKGROUND ART

L-tryptophan, an essential amino acid, has been widely used as a feed additive, a raw material for medical drugs such as infusion solutions, and a material for healthfoods, and has been produced by chemical synthesis, enzymatic reaction, fermentation, etc.

Recently, production of L-tryptophan is mainly carried out by microbial fermentation. In the initial stage of industrialization, analogue resistant strains obtained by chemical mutation have been mainly used. However, as gene recombination technologies rapidly developed in the 1990s and regulatory mechanisms were understood at the molecular level, the recombinant *E. coli* and *Corynebacterium* strains obtained by genetic engineering techniques have been mainly used.

The production of tryptophan by microorganisms starts with DAHP(3-deoxy-D-arobino-heptulosonate-7-phosphate) produced by the polymerization of PEP (PhospoEnolPyruvate) that is an intermediate of glycolysis, with E4P (erythrose-4-phosphate) that is an intermediate of the pentose phosphate pathway. Then, tryptophan is biosynthesized from chorismate through the common aromatic biosynthetic pathway. Specifically, tryptophan is synthesized by anthranilate synthase (EC 4.1.3.27) encoded by trpE gene, anthranilate synthase (EC 4.1.3.27) and anthranilate PRPP transferase (EC 2.4.1.28) encoded by trpD gene, indole-3-glycerol phosphate synthase (EC 4.1.1.48) and phosphoribosylanthranilate isomerase (EC 5.3.1.24) encoded by trpC gene, and tryptophan synthase (EC 4.2.1.20) encoded by trpB gene and trpA gene. The gene cluster trpEDCBA that mediates the above reaction is placed in the chromosome and have an operon structure containing a single regulatory region.

A tryptophan operon is actively transcribed so as to produce a sufficient amount of tryptophan required by the cell. However, if tryptophan level in the cell is high, a repressor binds to tryptophan and then the tryptophan operon is inactivated by the binding of the repressor to operon regulatory region, thereby the transcription is inhibited.

In addition, operons for biosynthesis of amino acids such as threonine, phenylalanine, leucine, tryptophan and histidine have another regulatory mechanism known as an attenuation (J Bacteriol. (1991) 173, 2328-2340). As is known in the art with respect to the attenuation, under conditions deficient in amino acids, the structure of the mRNA corresponding specific sequence region between the promoter and the first gene of the operon on the chromosome, changes to a structure advantageous for the translation process to promote the expression of biosynthetic genes, but under conditions rich in the amino acids, the short transcribed mRNA forms a three-dimensional structure, named "hairpin structure, to inhibit the translation process (J Biol Chem., (1988) 263:609-612).

In the initial stage of the development of L-tryptophan-producing strains, it was a major object to increase the efficiency of production through the enhancement of enzyme activity either by releasing the feedback inhibition of tryptophan biosynthesis pathway enzymes caused by the final product, tryptophan or by increasing the copy number of the tryptophan operon genes on the chromosome or in the form of vector in order to enhance the expression of tryptophan biosynthetic enzymes (Appl. Environ. Microbiol., (1982) 43:289-297; Appl. Microbiol. Biotechnol., (1993) 40:301-305; Trends Biotechnol., (1996) 14:250-256).

Methods for imparting the ability to produce L-tryptophan to microorganisms include a method of imparting resistance to tryptophan analogues or anthranilate as the intermediate product by chemical mutation, or a method of modifying microorganisms by genetic engineering. Examples of the chemical mutation method include those described in Korean Patent Registration No. 1987-0001813, Korean Patent Registration No. 0949312 and the like, and examples of the modification method based on genetic engineering include various approaches which use a strain obtained by enhancing the transketolase-encoding tktA gene or the galactose permease-encoding galP gene in the aromatic amino acid biosynthesis pathway to increase the supply of E4P (erythrose4-phosphate) or PEP (phosphoenolpyruvate) and reducing the feedback inhibition of DAHP (3-deoxy-D-arabino-heptulosonate-7-phosphate) in order to enhance the aromatic biosynthetic pathway (Trends Biotechnol., (1996) 14:250-256, Microbial Cell Factories (2009) 8:19), or a strain obtained by additionally introducing tryptophan operon genes into the vector or chromosome (Appl. Environ. Microbiol., (1982) 43:289-297, Appl. Microbiol. Biotechnol., (1993) 40:301-305).

However, even though the tryptophan operon was introduced with releasing the feedback inhibition of the biosynthetic enzymes, those approaches did not reached to an increase in the production yield of tryptophan, due to the regulatory mechanisms such as the inhibition or attenuation of the operon genes at transcription level.

DISCLOSURE

Technical Problem

The present inventors have developed a method of releasing the inhibition or attenuation of tryptophan operon genes at transcription level in an L-tryptophan-producing strain, and a method capable of enhancing tryptophan biosynthetic enzymes using the same. In addition, in order to solve the problem in that the production yield of tryptophan-producing strains does not increase because of anthranilate accumulation as the tryptophan operon is enhanced, the present inventors have constructed a tryptophan-producing strain which has increased production yield and low level of anthranilate accumulation by expressing the gene cluster other than the gene encoding anthranilate synthase(TrpE) among the tryptophan operon genes as a form which is desensitized a regulatory mechanism such as the feedback inhibition or inhibition mechanism It is an object of the present invention to provide a microorganism of the genus *Escherichia* having enhanced L-tryptophan productivity by modifying so as to desinsitize the inhibition or attenuation of the tryptophan operon and reduce the accumulation of anthranilate.

Another object of the present invention is to provide a method of producing L-tryptophan using the microorganism of the genus *Escherichia*.

Technical Solution

In order to accomplish the above objects, an embodiment of the present invention provides a recombinant microorganism of the genus *Escherichia* having enhanced L-tryptophan productivity which has been modified to delete a part or all of a leader peptide having a nucleotide sequence represented by SEQ ID NO: 2 in an expression regulatory region having a nucleotide sequence represented by SEQ ID NO: 1 on an endogenous tryptophan operon.

Another embodiment of the present invention also provides a method for producing L-tryptophan, comprising culturing the above-described recombinant microorganism of the genus *Escherichia*.

Advantageous Effects

The recombinant microorganism produced according to the present invention eliminates the excessive accumulation of anthranilate therein and can be advantageously used to produce L-tryptophan in high yield.

A) Tryptophan operon genes, and a regulatory region thereof in the *E. coli* chromosome(Ptrp);

B) A Ptrp form;

C) A form that the trpL gene encoding leader peptide is deleted (DtrpL); and

D) A form that the trpL gene encoding the leader peptide and the attenuator are deleted (Dtrp_att).

Figure 2:
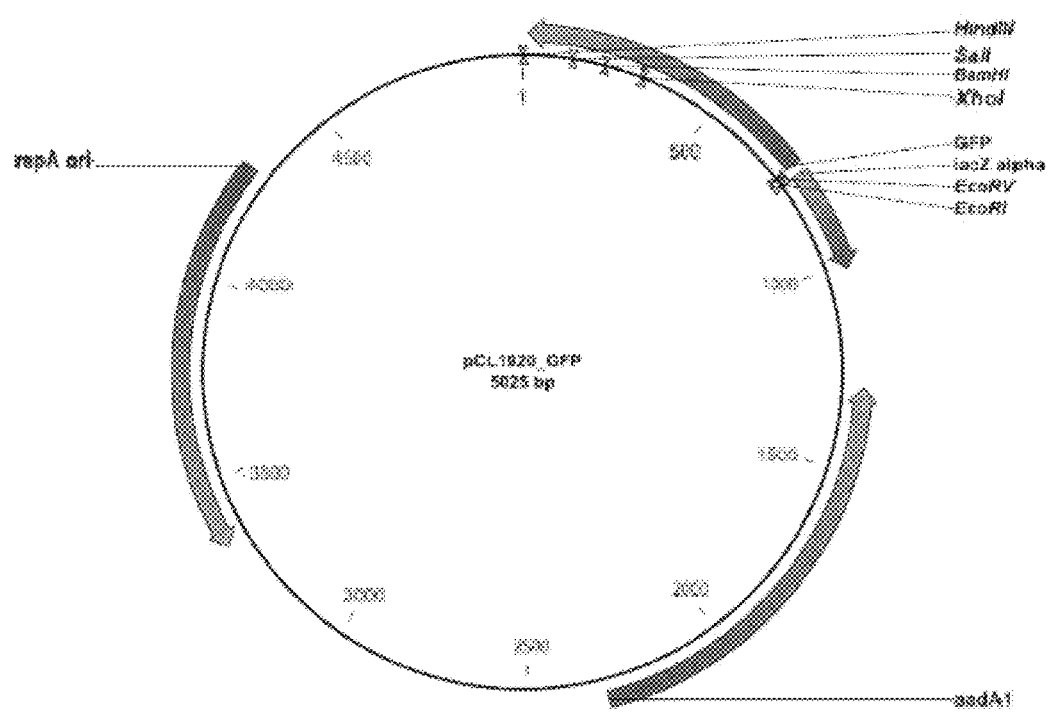

FIG. 2 shows a pCL-GFP vector used to measure the intensity of an expression regulatory region of the tryptophan operon.

Figure 3:
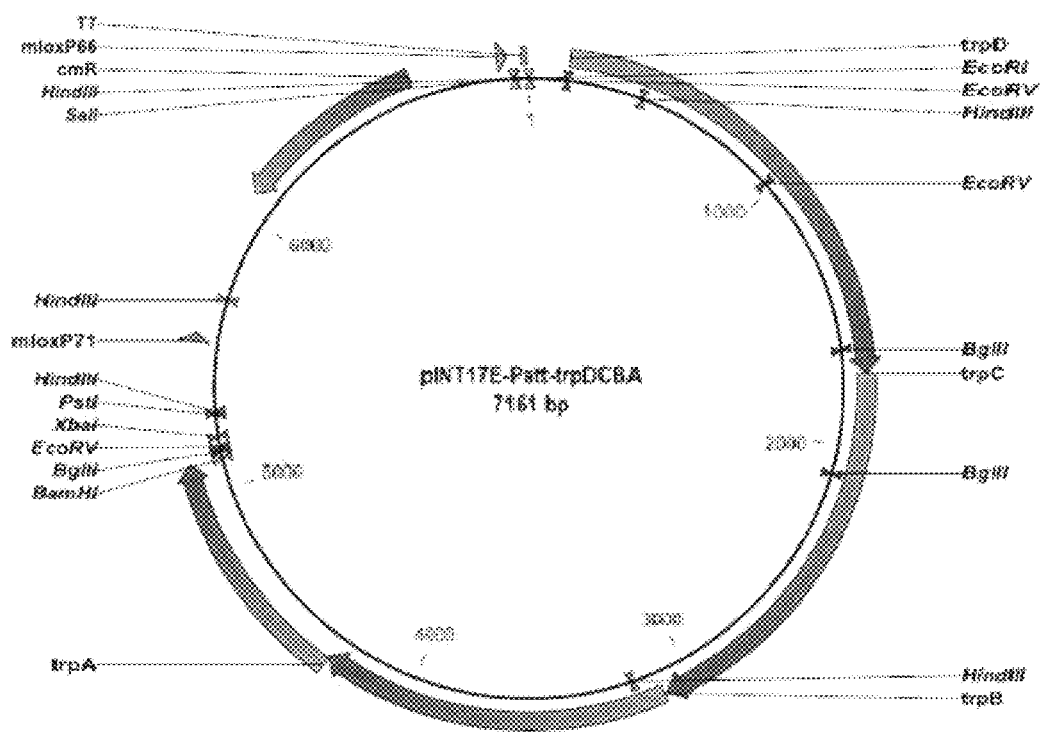

FIG. 3 shows the vector pINT17E-Patt-trpDCBA for introducing the tryptophan biosynthetic genes trpDCBA into the chromosome to increase the copy number of the genes.

MODE FOR INVENTION

Hereinafter, the present invention will be described in detail.

An embodiment of the present invention provides a recombinant microorganism of the genus *Escherichia* having enhanced L-tryptophan productivity, which has been modified to delete part or all of a leader peptide having a nucleotide sequence represented by SEQ ID NO: 2 in an expression regulatory region having a nucleotide sequence represented by SEQ ID NO: 1 on an endogenous tryptophan operon.

As used herein, the term "tryptophan operon" or "Trp operon" means the entire operon including all the trpEDCBA genes. The tryptophan operon has a nucleotide sequence represented by SEQ ID NO: 9.

An L-tryptophan-producing microorganism that may be used in the present invention may be any prokaryotic or eukaryotic microorganism as long as they have a L-tryptophan productivity. Examples of this microorganism may include microorganisms belonging to the genus *Escherichia*, the genus *Erwinia*, the genus *Serratia*, the genus *Providencia*, the genus *Corynebacterium* and the genus *Brevibacterium*. The microorganism is specifically a microorganism belonging to the genus *Escherichia*, and more specifically *E. coli*. Most specifically, the *E. coli* strain of the present invention may be a strain obtained by enhancing the activities of tryptophan biosynthetic enzymes such as anthranilate synthase (TrpE), anthranilate PRPP transferase (TrpD), phosphoribosyl anthranilate isomerase (TrpC) or tryptophan synthase (TrpA, TrpB) while maintaining 3-deoxy-D-arabino-heptulosonate 7-phosphate synthase (aroG) which is released for feedback inhibition, enhancing the activities of aromatic biosynthesis pathway enzymes such as 3-dehydroquinate synthetase(AroB), shikimate dehydrogenase (AroE), shikimate kinase (AroL), 5-enolpyruvylshikimate-3-phosphate synthase (AroA) or chorismate synthase (AroC), enhancing the activity of phosphoglycerate dehydrogenase (SerA) or transketolase (TktA) to enhance the supply of the intermediates, serine and PRPP, of the tryptophan biosynthesis pathway. Furthermore, the *E. coli* strain of the present invention may be a strain obtained by inactivating the activities of prephenate dehydratase and chorismate mutase (PheA) in the aromatic biosynthesis pathway or inactivating the activities of prephenate dehydrogenase, chorismate mutase (tyrA), tryptophanase (tnaA) and tryptophan transporter (tnaB, mtr).

More specifically, the recombinant microorganism of the present invention is recombinant *E. coli* strain CA04-2004 (accession number: KCCM11246P).

As used herein, the term "expression regulatory region" of the endogenous tryptophan operon means a region including a promoter, a leader peptide and an endogenous attenuator. Specifically, the expression regulatory region has a nucleotide sequence represented by SEQ ID NO: 1.

As used herein, the term "leader peptide" means a low-molecular-weight peptide that is encoded by the upstream leader sequence of the start codon of the gene. Specifically, the leader peptide has a nucleotide sequence represented by SEQ ID NO: 2, and a polypeptide that is expressed by the leader peptide may be an amino acid sequence represented by SEQ ID NO: 4. This leader peptide functions to form the hairpin structure when the concentration of tryptophan is high, thereby promoting the structure-formation of the endogenous attenuator to terminate the transcription of tryptophan biosynthetic genes.

As used herein, the term "delete" means removing part or all of either a nucleotide sequence from the start codon to the stop codon of the target gene, or the nucleotide sequence of a regulatory region thereof, from the chromosome.

An aspect of the present invention also provides a recombinant microorganism of the genus *Escherichia*, which further has been modified to delete part or all of an endogenous attenuator having a nucleotide sequence represented by SEQ ID NO: 3 so as to enhance its ability to produce L-tryptophan.

As used herein, the term "endogenous attenuator" means a region having a nucleotide sequence represented by SEQ ID NO: 3, which excludes the promoter and the leader peptide in the expression regulatory region that causes the attenuation mechanism.

An aspect of the present invention also provides a microorganism of the genus *Escherichia*, which further has been modified to enhance activities of proteins that are encoded by the tryptophan operon.

An aspect of the present invention also provides a microorganism of the genus *Escherichia*, which further has been modified to enhance activities of proteins that are encoded by the tryptophan biosynthetic gene cluster trpDCBA excluding the trpE gene encoding anthranilate synthase.

As used herein, the term "tryptophan biosynthetic gene cluster" means a gene cluster consisting of a combination of two or more of trpD, trpC, trpB and trpA that are tryptophan operon genes. Specifically, the tryptophan biosynthetic gene cluster may be a trpDCBA gene cluster having a nucleotide sequence represented by SEQ ID NO: 10. Herein, the trpD gene encodes a protein having an amino acid sequence represented by SEQ ID NO: 37; the trpC gene encodes a protein having an amino acid sequence represented by SEQ ID NO: 38; the trpB gene encodes a protein having an amino acid sequence represented by SEQ ID NO: 39; and the trpA gene encodes a protein having an amino acid sequence represented by SEQ ID NO: 40.

Enhancing the activity of the tryptophan biosynthetic gene cluster except for anthranilate synthase that is encoded by the trpE gene of the tryptophan operon is performed to solve the problem which the production yield of tryptophan does not increase due to accumulation of anthranilate as the tryptophan operon is enhanced.

Methods for enhancing the expression of the genes include: 1) a method of increasing the chromosomal or intracellular copy number of the genes; or 2) a method of replacing the chromosomal promoter of the genes with a strong exogenous promoter or modifying the chromosomal promoter to a strong promoter.

Examples of the method of increasing the copy number include a method of introducing the gene into a vector to enhance the expression of the gene. Examples of a vector that may be used in the present invention include plasmid vectors such as pBR, pUC, pBluescriptll, pGEM, pTZ, pCL and pET-type plasmids. Vectors that may be used in the present invention are not particularly limited to, and any known expression vectors may be used. Specifically, pACYC177, pACYC184, pCL, pECCG117, pUC19, pBR322 or pMW118 vectors may be used. Most specifically, pACYC177, pCL and pCC1BAC vectors may be used.

Meanwhile, examples of an exogenous promoter that may be used in the present invention include, but are not limited to, known promoters such as trc, lac and tac promoters. In addition, modifying the chromosomal promoter to a strong promoter can be performed by deleting part or all of the leader peptide and/or further deleting part or all of the endogenous attenuator as described above, but is not limited thereto.

In a specific embodiment of the present invention, a recombinant L-tryptophan-producing microorganism of the genus *Escherichia* was produced by deleting part or all of the leader peptide having a nucleotide sequence represented by SEQ ID NO: 2 in the expression regulatory region having a nucleotide sequence represented by SEQ ID NO: 1 on the endogenous tryptophan operon, and deleting part or all of the endogenous attenuator having a nucleotide sequence represented by SEQ ID NO: 3 so as to increase the ability to produce L-tryptophan. In addition, the recombinant L-tryptophan-producing microorganism was produced by further enhancing the activities of the proteins having an amino acid sequence represented by SEQ ID NOS: 37, 38, 39 and 40, which are encoded by the tryptophan biosynthetic gene cluster trpDCBA excluding the trpE gene encoding anthranilate synthase. The produced recombinant microorganism was deposited as the accession number KCCM11246P.

Another embodiment of the present invention also provides a method for producing L-tryptophan, comprising culturing recombinant L-tryptophan-producing microorganism of the genus *Escherichia* having enhanced L-tryptophan productivity.

In a specific aspect, the present invention provides a method comprising culturing a recombinant L-tryptophan-producing microorganism of the genus *Escherichia* having enhanced L-tryptophan productivity, which has been modified to delete part or all of the leader peptide having a nucleotide sequence represented by SEQ ID NO: 2 in the expression regulatory region having a nucleotide sequence represented by SEQ ID NO: 1 on an endogenous tryptophan operon and to delete part or all of the endogenous attenuator having a nucleotide sequence represented by SEQ ID NO: 3 so as to increase the ability to produce L-tryptophan, and further to enhance the activities of the proteins which is encoded by the tryptophan operon by enhancing the expression of tryptophan biosynthetic gene cluster trpDCBA excluding the trpE gene encoding anthranilate synthase.

The media and culture conditions that are used in culture of the microorganism of the present invention may be any of those that are used in culture of microorganisms belonging to the genus *Escherichia*, but these should suitably satisfy the requirements of the microorganism of the present invention. Specifically, the microorganism of the present invention may be cultured in a conventional medium containing suitable carbon sources, nitrogen sources, amino acids, vitamins and the like under aerobic conditions while adjusting temperature, pH and the like.

Carbon sources that may be used in the present invention include carbohydrates such as glucose, fructose, sucrose, maltose, mannitol, sorbitol; alcohols such as sugar alcohol, glycerol, pyruvic acid, lactic acid and citric acid; and amino acids such as organic acid, glutamic acid, methionine and lysine. In addition, natural organic nutrient sources such as starch hydrolysates, molasses, blackstrap molasses, rice bran, cassava, bagasse and corn steep liquor may be used. Specifically, carbohydrates such as glucose and sterile pretreated molasses (i.e., molasses converted to reduced sugars) may be used. In addition, suitable amounts of other carbon sources may be used without limitation.

Nitrogen sources that may be used in the present invention include inorganic nitrogen sources such as ammonia, ammonium sulfate, ammonium chloride, ammonium acetate, ammonium carbonate, and ammonium nitrate; amino acids such as glutamic acid, methionine and glutamine; and organic nitrogen sources such as peptone, NZ-amine, meat extract, yeast extract, malt extract, corn steep liquor, casein hydrolysate, fish meal or its digested product, defatted soybean cake or its digested product, etc. These nitrogen sources may be used alone or in combination.

The medium may contain, as phosphorus sources, potassium phosphate monobasic, potassium phosphate dibasic and corresponding sodium-containing salts. Inorganic compounds that may be used in the present invention include sodium chloride, calcium chloride, iron chloride, magnesium sulfate, iron sulfate, manganese sulfate and calcium carbonate. In addition, the medium may contain amino acids, vitamins and suitable precursors. These sources or precursors may be added to the medium in a batch or continuous manner.

Compounds such as ammonium hydroxide, potassium hydroxide, ammonia, phosphoric acid and sulfuric acid may be added to the medium in a suitable manner during culture to adjust the pH of the culture medium. In addition, during the culture, a antifoaming agent such as fatty acid polyglycol ester may be used to suppress the formation of bubbles. Further, in order to maintain the culture medium in an aerobic state, oxygen or oxygen-containing gas may be injected into the culture medium. In addition, in order to maintain the culture medium in an anaerobic or non-aerobic state, no gas is injected, or nitrogen, hydrogen or carbon dioxide gas may be injected into the culture medium.

The culture medium is typically maintained at a temperature ranging from 27° C. to 37° C., and specifically from 30° C. to 35° C. Culture of the microorganism may be continued until the desired level of the useful substance will be obtained. Specifically, the culture period is may be 10-100 hours.

The method of the present invention may further comprise purifying or recovering the L-amino acid produced in the culture step. The purification or recovery process may be performed by purifying or recovering the desired L-amino acid from the culture medium using a suitable method, for example, a batch, continuous or fed-batch culture method.

Hereinafter, the present invention will be described in further detail with reference to examples. It is to be understood, however, that these examples are for illustrative purposes and are not intended to limit the scope of the present invention.

EXAMPLES

Example 1

Figure 1:
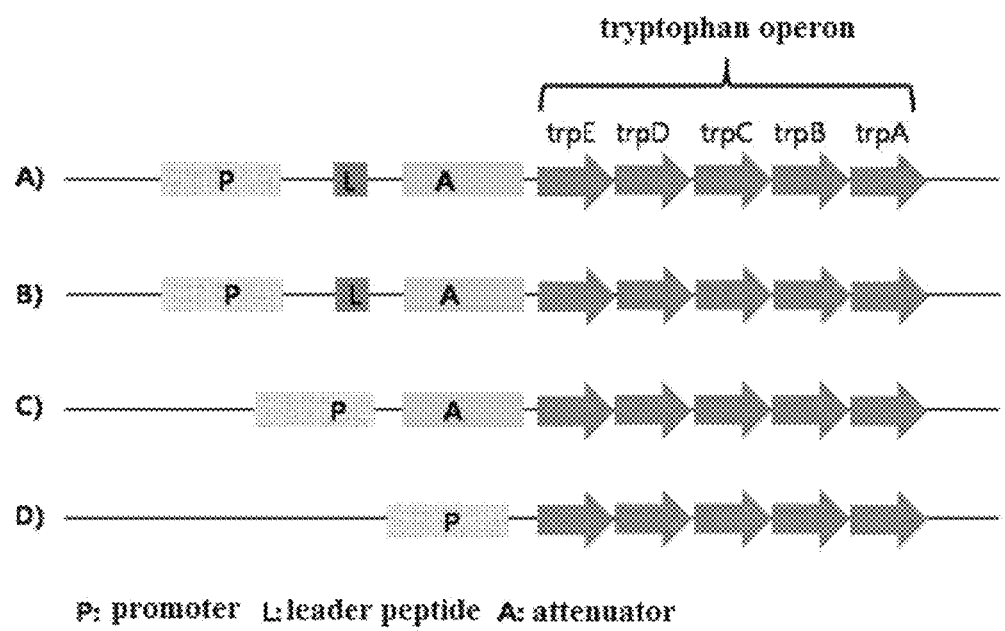
FIG. 1 shows a schematic view representing the tryptophan operon genes, a regulatory region for the genes in the *E. coli* chromosome, and the deletion form of the gene described in the present invention.

Construction of a Fusion Vector Comprising GFP and an Expression Regulatory Region from which a Leader Peptide was Removed, in Order to Release an Expression Regulation for Tryptophan Biosynthesis As shown in FIG. 1, in order to amplify an expression regulatory region comprising a deletion of the trpL gene encoding a leader peptide (L) (the expression regulatory region is hereinafter referred to as "DtrpL", corresponding to FIG. 1C) in an expression regulatory region of the tryptophan operon which is composed of a promoter (P), the leader peptide (L) and an attenuator (A), polymerase chain reaction (hereinafter referred to as "PCR") was performed using the chromosomal DNA of an E. coli W3110 strain (purchased from the American Type Culture Collection (ATCC); GenBank accession number AC000091) as a template.

Specifically, a 155 bp fragment having a KpnI restriction enzyme site in the 5' region was amplified by PCR with Pfu polymerase using primers 1 and 2 under the following conditions: 30 cycles, each consisting of denaturation at 94 t for 1 min, annealing at 58° C. for 30 sec, and extension at 72 t for 30 sec. Meanwhile, a 105 bp fragment having an EcoRV restriction enzyme site in the 3' region was amplified by PCR using primers 3 and 4 under the above-described conditions. The obtained DNA fragments were recovered using GeneAll® Expin™ GEL SV kit (Seoul, Korea), and then used as a template for crossover PCR.

In order to make the DtrpL, crossover PCR was performed using the two DNA fragments as a template and primers 1 and 4. Specifically, a 245 bp fragment (SEQ ID NO: 5) was amplified by PCR under the above-described conditions. The amplified fragment was treated with the restriction enzymes KpnI and EcoRV, and then ligated with pCL1920GFP (SEQ ID NO: 8) which was treated with the same restriction enzymes, thereby constructing pCL-DtrpL_GFP.

In order to amplify an expression regulatory region comprising a deletion of the genes encoding the leader peptide (L) and the attenuator (A) (the expression regulatory region is hereinafter referred to as "Dtrp_att") in the expression regulatory region of the tryptophan operon, a 148 bp fragment (SEQ ID NO: 6) having a KpnI restriction enzyme site in the 5' region and an EcoRV restriction enzyme site in the 3' region was amplified by PCR using the chromosomal DNA of the E. coli W3110 strain as a template and primers 1 and 5. The amplified fragment was treated with the restriction enzymes KpnI and EcoRV, and then ligated with pCL1920GFP which was treated with the same restriction enzymes, thereby constructing pCL-Dtrp_att-GFP.

In addition, in order to make a vector having a wild-type expression regulatory region for use as a control in subsequent experiments, a 290 bp fragment having a KpnI restriction enzyme site in the 5' region and an EcoRV restriction enzyme site in the 3' region was amplified by PCR using the chromosomal DNA of the E. coli W3110 strain as a template and primers 1 and 4. The amplified fragment was treated with the restriction enzymes KpnI and EcoRV, and then ligated with pCL1920GFP which was treated with the same restriction enzymes, thereby constructing pCL-Ptrp-GFP.

```
Primer 1:
                                    (SEQ ID NO: 11)
5' TTAGGTACCGGCGCACTCCCGTTCTGGATA 3';

Primer 2:
                                    (SEQ ID NO: 12)
5' ACTGCCCGTTGTCGATACCCTTTTTACGT 3';

Primer 3:
                                    (SEQ ID NO: 13)
5' TCGACAACGGGCAGTGTATTCACCATG 3';

Primer 4:
                                    (SEQ ID NO: 14)
5' AATGATATCTGTTATTCTCTAATTTTGTT 3';

Primer 5:
                                    (SEQ ID NO: 15)
5' AATGATATCACCCTTTTTACGTGAACTTG 3'.
```

Example 2

Measurement of Expression Level of GFP

Each of the pCL-DtrpL_GFP, pCL-Dtrp_att-GFP and pCL-Ptrp GFP vectors prepared in Example 1 was transformed into wild-type E. coli W3110 and the tryptophan-producing strain E. coli KCCM10812P, and then the intensities of GFP in the strains were measured.

The parent strain E. coli KCCM10812P (Korean Patent Registration No. 10-0792095) used in this Example is a strain derived from an E. coli variant having L-phenylalanine productivity (KFCC 10066, Korean Patent Publication No. 1985-0001232). Specifically, KCCM10812P is a recombinant *E. coli* strain having L-tryptophan productivity, wherein the strain has been modified to recover tryptophan auxotrophy, to inactivate the pheA, trpR, mtr and tnaAB genes, and to mutate the aroG and trpE genes.

Specifically, each of the strains was inoculated into 25 ml of M9 medium (containing 0.5% glucose+2 g/L yeast extract and further containing 0.1 g/L tyrosine and 0.1 g/L phenylalanine in the case of KCCM10812) in a 250 ml flask at a volume ratio of 1/100 (v/v) and cultured at 37° C. until a predetermined OD was reached. The cultured strains were recovered by centrifugation and washed once with 1×TE, and GFP therein was measured using Synergy HT Multi-Mode Microplate Reader (Biotek, USA).

The results of the measurement are shown in Table 1 below. OD1 and OD3 in Table 1 indicate the OD values measured at 600 nm using UV mini-1240 spectrophotometer (Shimadzu) after diluting each of the culture products to a suitable concentration.

As shown in FIG. 1, in the case of the wild-type W3110 strain, with respect to that of Ptrp as 1, the relative intensity of Dtrp_att (comprising a deletion of the leader peptide and the attenuator) was about 7 fold at an OD value of 1 (OD1) and 10 fold at an OD value of 3 (OD3), and the relative intensity of DtrpL comprising a deletion of only the leader peptide was about 1.5-2 fold higher than that of the wild-type regulatory region (Ptrp). In comparison with this, in the case of the L-tryptophan-producing strain KCCM 10812P, with respect to that of Ptrp taken as 1, the relative intensity of Dtrp_att (comprising a deletion of the leader peptide and the attenuator) was about 19 fold at an OD value of 1 (OD1) and 27 fold at an OD value of 3 (OD3), and the relative intensity of DtrpL comprising a deletion of only the leader peptide was about 4 fold higher than that of the wild-type regulatory region (Ptrp). Such results indicate that the deletion of the leader peptide or the attenuator leads to an increase in expression, even though this increase in expression in the wild-type strain is weaker than in the L-tryptophan producing strain.

TABLE 1

| Strain | Promoter | GFP measurement (fold) | |
| --- | --- | --- | --- |
| | | OD1 | OD3 |
| W3110 | Dtrp_att | 6.5 ± 0.7 | 9.6 ± 1.1 |
| | DtrpL | 1.5 ± 0.2 | 2.4 ± 0.3 |
| | Ptrp | 1 | 1 |
| KCCM10812P | Dtrp_att | 18.9 ± 1.3 | 27 ± 2.0 |
| | DtrpL | 3.8 ± 0.5 | 3.9 ± 0.8 |
| | Ptrp | 1 | 1 |

Example 3

Construction of Vectors Having Tryptophan Operon (trpEDCEA) Whose Expression Regulatory Region was Replaced Based on the results of Example 2, in order to construct an *E. coli* strain whose tryptophan operon genes were enhanced using a vector, a 6564 bp fragment (SEQ ID NO: 9) was amplified using the chromosomal DNA of the parent strain *E. coli* KCCM10812P as a template and primers 6 and 7 under the above-described PCR conditions.

The amplified DNA fragment was recovered using Gene-All® Expin™ GEL SV kit (Seoul, Korea), and then treated with the restriction enzymes EcoRV and HindIII. For cloning with the prepared DNA fragment, each of the pCL-Dtrp_att-GFP, pCL-DtrpL_GFP and pCL-Ptrp_GFP vector was treated with EcoRV and HindIII to remove the GFP region, thereby obtaining 4291 bp fragments. Each of the prepared vectors was ligated with the insert, and then introduced into *E. coli* DH5a by transformation, thereby constructing pCL-Dtrp_att-trpEDCBA, pCL-DtrpL_trpEDCBA and pCL-Ptrp_trpEDCBA vectors.

Primer 6:
(SEQ ID NO: 16)
5' CCCGATATCATGCAAACACAAAAACCGAC 3';

Primer 7:
(SEQ ID NO: 17)
5' GGGAAGCTTAAAGGATCCGTGGGATTAACTGCGCGTCGCCGCT TT 3'.

Example 4

Construction of Vectors Whose Expression Regulatory Region was Replaced and which Had Tryptophan Biosynthetic Gene Cluster (trpDCRA) Excluding trpE In order to construct vectors by replacing the GFP region of the pCL-Dtrp_att-GFP, pCL-DtrpL_GFP and pCL-Ptrp_GFP vectors prepared in Example 1 with trpDCBA, each of the pCL Dtrp_att-GFP, pCL-DtrpL_GFP and pCL-Ptrp_GFP vectors was treated with EcoRV and HindIII to remove the GFP region, thereby obtaining 4291 bp fragments.

Then, in order to construct *E. coli* strains whose the trpDCBA genes of the tryptophan operon were enhanced using a vector, a 5002-bp fragment (SEQ ID NO: 10) was amplified by PCR using the chromosomal DNA of the parent strain *E. coli* KCCM10812P as a template and primers 7 and 8.

The amplified DNA fragment was recovered using Gene-All® Expin™ GEL SV kit (Seoul, Korea), and then treated with the restriction enzymes EcoRV and HindIII. The prepared vector and insert were ligated with each other, and then introduced into *E. coli* DH5a by transformation, thereby constructing pCL-Dtrp_att-trpDCBA, pCL-DtrpL_trpDCBA and pCL-Ptrp_trpDCBA vectors.

Primer 8:
(SEQ ID NO: 18)
5' AAAGATATCATGGCTGACATTCTGCTGCT 3'.

Example 5

Construction of Vectors Having Low Copy Number of Tryptophan Operon Genes Having Various Expression Regulatory Regions A typical vector that is expressed with low copy number in *E. coli* is pCC1BAC (Epicentre, USA). In order to express the tryptophan operon genes with low copy number using this vector, the pCL-Dtrp_att-trpEDCBA, pCL-DtrpL_trpEDCBA, pCL-Ptrp_trpEDCBA, pCL-Dtrp_att-trpDCBA, pCL-DtrpL_trpDCBA and pCL-Ptrp_trpDCBA prepared in Examples 3 and 4 were digested with the restriction enzyme HindIII.

The resulting DNA fragments were electrophoresed on agarose, and then cut according to their size and recovered using GeneAll® Expin™ GEL SV kit (Seoul, Korea). Next, each of the fragments was ligated with the pCC1BAC vector (digested at the HindIII site), and then introduced into *E. coli* DH5a by transformation.

Each of the transformed strains was smeared on LB Cm solid medium (LB+chloramphenicol agar plate), and strains having Cm resistance were selected, thereby constructing pBAC-Dtrp_att-trpEDCBA, pBAC-DtrpL_trpEDCBA, pBAC-Ptrp_trpEDCBA, pBAC-Dtrp_att-trpDCBA, pBAC-DtrpL_trpDCBA and pBAC-Ptrp_trpDCBA vectors.

Example 6

Construction of *E. coli* Strain in which pheA Gene was Inactivated

In order to construct a strain close to a tryptophan-producing strain from the wild type *E. coli* W3110 strain, the pheA gene (NCBI gene ID: 12934467) encoding chorismate mutase/prephenate dehydratase (CM-PDT) was inactivated by deletion through homologous recombination. CM-PDT is an enzyme in the first step of producing phenylalanine from chorismate, and deletion of the pheA gene was used to inhibit the phenylalanine biosynthesis pathway. For this deletion, the one-step inactivation method (developed by Datsenko K A et al.), mutagenesis technique using lambda red recombinase, was used (One-step inactivation of chromosomal genes in *Escherichia coli* K-12 using PCR products, Datsenko K A, Wanner B L., Proc Natl Acad Sci USA. 2000 Jun. 6; 97(12):6640-5). As a marker for confirming insertion into the genes, the chloramphenicol-resistant gene of pUCprmfmloxC was used (Korean Patent Laid-Open Publication No. 2009-0075549).

An about 1200 bp gene fragment was amplified by PCR using the vector pUCprmfmloxP as a template and primers 9 and 10, which have a portion of the pheA gene and a portion of the nucleotide sequence of the chloramphenicol-resistant gene of the pUCprmfmloxP vector.

Primer 9:
(SEQ ID NO: 19)
5'-GGCCTCCCAAATCGGGGGGCCTTTTTTATTGATAACAAAAAGGCA
ACACTAGGTGACACTATAGAACGCG-3';

Primer 10:
(SEQ ID NO: 20)
5'-AACAGCCCAATACCTTCATTGAACGGGTGATTTCCCCTAACTCTT
TCAATTAGTGGATCTGATGGGTACC-3'.

The DNA fragment obtained by PCR amplification was electrophoresed on 0.8% agarose gel, and then eluted and used as a template in secondary PCR. Secondary PCR was performed so that the 5' and 3' regions of the primary DNA fragment had 20 pairs of complementary nucleotide bases. In addition, an about 1300 bp gene fragment was amplified by PCR using the eluted primary PCR product as a template and primers 11 and 12, which include the 5' and 3' regions of the pheA gene. The resulting DNA fragment was electrophoresed on 0.8% agarose gel, and then eluted and used in recombination.

Primer 11:
(SEQ ID NO: 21)
5'-GAATGGGAGGCGTTTCGTCGTGTGAAACAGAATGCGAAGACGAAC
AATAAGGCCTCCCAAATCGGGGGGC-3';

Primer 12:
(SEQ ID NO: 22)
5-GGCACCTTTTCATCAGGTTGGATCAACAGGCACTACGTTCTCACTT
GGGTAACAGCCCAATACCTTCATT-3'.

According to the method developed by Datsenko K A et al., the W3110 *E. coli* strain transformed with the pKD46 vector was made as competent status, and then transformed with the 1300 bp gene fragment obtained by PCR. The strain having resistance to chloramphenicol was selected on LB medium. PCR was performed using primers 13 and 14, and the PCR amplification product had a size of about 2500 bp, indicating that the pheA gene was deleted in the strain.

Primer 13:
(SEQ ID NO: 23)
5'-TTGAGTGTATCGCCAACGCG-3';

Primer 14:
(SEQ ID NO: 24)
5'-AAAGCCGCGTGTTATTGCGT-3'.

The pKD46 vector was removed from the primary recombinant strain having chloramphenicol resistance, and then a pJW168 vector was introduced into the strain, and the chloramphenicol marker gene was removed from the strain (Gene, (2000) 247, 255-264). The resulting strain was an about 500 bp amplification product obtained by PCR using primers 13 and 14, indicating that the target gene deletion was achieved. The constructed strain was named "*E. coli* W3110 trpΔ1".

Example 7

Construction of *E. coli* Strain from which tnaAB Gene was Inactivated

From the *E. coli* W3110 trpΔ1 strain constructed in Example 6, the tnaAB operon (NCBI gene ID: 12933600, 12933602) consisting of the tnaA gene encoding tryptophanase and the tnaB gene encoding tryptophan importer was deleted by homologous recombination. Due to this deletion, the degradation pathway of tryptophan after its production can be blocked, and the influx of tryptophan which is secreted to the medium into the cells can be prevented, thereby imparting the properties of tryptophan-producing strains. For this deletion, an about 1200 bp gene fragment was amplified by PCR in the same manner as described in Example 6 using the vector pUCprmfmloxP as a template together with primers 15 and 16, which have a portion of the tnaAB gene and a portion of the nucleotide sequence of the chloramphenicol-resistant gene of the pUCprmfmloxP vector. In addition, the DNA fragment obtained by PCR amplification was further amplified by PCR in the same manner as described in Example 6 using primers 17 and 18, thereby obtaining a 1300 bp gene fragment.

Primer 15:
(SEQ ID NO: 25)
5'-TTAGCCAAATTTAGGTAACACGTTAAAGACGTTGCCGAACCAGCA
CAAAAAGGTGACACTATAGAACGCG-3'

Primer 16:
(SEQ ID NO: 26)
5'-ATGAAGGATTATGTAATGGAAAACTTTAAACATCTCCCTGAACCG
TTCCGTAGTGGATCTGATGGGTACC-3';

Primer 17:
(SEQ ID NO: 27)
5'-TGATTTCCTGAGAGGCAAGAAGCCAGCGAATGGCTGGCTTCTTGA
AGGATTTAGCCAAATTTAGGTAACA-3';

Primer 18:
(SEQ ID NO: 28)
5'-AATCGGTATAGCAGATGTAATATTCACAGGGATCACTGTAATTAA
AATAAATGAAGGATTATGTAATGGA-3'.

In order to delete the tnaAB genes, the E. coli strain W3110 trpΔ1 that the vector pKD46 was introduced was made competent was constructed in the same manner described in Example 6, and then the 1300 bp gene fragment obtained by PCR was transformed into the E. coli strain. The strain having resistance to chloramphenicol was selected on LB medium. PCR was performed using primers 19 and 20, and the PCR amplification product had a size of about 5400 bp, indicating that the tnaAB genes were deleted in the strain.

Primer 19:
(SEQ ID NO: 29)
5'-CGGGATAAAGTAAAACCAGG-3';

Primer 20:
(SEQ ID NO: 30)
5'-CGGCGAAGGTAAGTTGATGA-3'.

The pKD46 vector was removed from the primary recombinant strain having chloramphenicol resistance in the same manner described in Example 6, and then the chloramphenicol marker gene was removed from the strain. The resulting strain was an about 550 bp amplification product obtained by PCR using primers 19 and 20, indicating that the desired gene deletion was achieved. The constructed strain was named "E. coli W3110 trpΔ2".

Example 8

Identification of L-Tryptophan Productivity of Strains Having Tryptophan Operon Having Various Expression Patterns The E. coli strains transformed with the vectors prepared according to the methods described in Examples 3, 4 and 5. The effects of the E. Coli variant were evaluated using W3110 trpΔ2 prepared in Examples 6 and 7 as a parent strain, and its carbon source was glucose.

In order to evaluate the titer, each strain was inoculated by a platinum loop and cultured overnight on LB solid medium. Then, one platinum loop of each strain was inoculated into 25 mL of glucose-containing medium, the composition of the medium is shown in Table 2 below. After inoculation, each strain was incubated at 37° C. and 200 rpm for 48 hours. The results are shown in Table 3 below. All the results were recorded as the average of three flask results.

TABLE 2

| Composition | Concentration (per liter) |
| --- | --- |
| Glucose | 2 g |
| KH2PO$_4$ | 1 g |
| (NH$_4$)$_2$SO$_4$ | 12 g |
| NaCl | 1 g |
| Na$_2$HPO$_4$•H$_2$O | 5 g |
| MgSO$_4$•H$_2$O | 1 g |
| MnSO$_4$•H$_2$O | 15 mg |
| CuSO$_4$•H$_2$O | 3 mg |
| ZnSO$_4$•H$_2$O | 30 mg |
| Sodium citrate | 1 g |
| Yeast extract | 1 g |
| Phenylalanine | 0.15 g |
| pH | 6.8 |

TABLE 3

| Parent strain | | Vector | L-tryptophan (g/L)** | Anthranilate (mg/L)** |
| --- | --- | --- | --- | --- |
| W3110 trp Δ2 | pCL1920 | pCC1BAC | 0.1 | 13 |
| | pCL-Ptrp_trpEDCBA | pBAC-Ptrp_trpEDCBA | 0.4 | 56 |
| | | pBAC-DtrpL_trpEDCBA | 0.4 | 53 |
| | | pBAC-Dtrp_att-trpEDCBA | 0.5 | 61 |
| | pCL-DtrpL_trpEDCBA | pBAC-Ptrp_trpEDCBA | 0.4 | 68 |
| | | pBAC-DtrpL_trpEDCBA | 0.5 | 73 |
| | | pBAC-Dtrp_att-trpEDCBA | 0.4 | 74 |
| | pCL-Dtrp_att-trpEDCBA | pBAC-Ptrp_trpEDCBA | 0.6 | 89 |
| | | pBAC-DtrpL_trpEDCBA | 0.5 | 95 |
| | | pBAC-Dtrp_att-trpEDCBA | 0.7 | 98 |
| | pCL-Ptrp-trpEDCBA | pBAC-Ptrp_trpEDCBA | 0.5 | 34 |
| | | pBAC-DtrpL_trpEDCBA | 0.6 | 35 |
| | | pBAC-Dtrp_att-trpEDCBA | 0.6 | 40 |
| | pCL-DtrpL-trpEDCBA | pBAC-Ptrp_trpDCBA | 0.5 | 45 |
| | | pBAC-DtrpL_trpDCBA | 0.5 | 42 |
| | | pBAC-Dtrp_att-trpDCBA | 0.6 | 38 |
| | pCL-Dtrp_att-trpEDCBA | pBAC-Ptrp_trpDCBA | 0.7 | 36 |
| | | pBAC-DtrpL_trpDCBA | 0.8 | 28 |
| | | pBAC-Dtrp_att-trpDCBA | 1.0 | 29 |

As can be seen from the results in Table 3 above, in the case in which the parent strain E. coli W3110 trpΔ2 was transformed with a combination of various vectors, if only the tryptophan operon was continuously enhanced, no positive effect on the production yield of tryptophan appeared while anthranilate accumulated. On the contrary, the strain modified to enhance the Trp operon and trpDCBA showed a positive effect on the production yield of tryptophan together with a decrease in the accumulation of anthranilate, compared to the strain in which only tryptophan operon was enhanced. Thus, it was confirmed that a decrease in the accumulation of anthranilate is an effective way to increase the production yield of L-tryptophan in tryptophan-producing strains.

Example 9

Identification of L-Tryptophan Productivity of Strains Having Tryptophan Operon Having Various Expression Patterns The vectors constructed according to the methods described in Examples 3, 4 and 5 were introduced into the L-tryptophan-producing parent strain E. coli KCCM10812P according to the combination shown in Table 5 below. The titers of the strains were evaluated using glucose as a carbon source. As a result, it appeared that not only the enhancement of trpDCBA, but also the enhancement of the tryptophan operon, is important, similar to the results of Example 8. Thus, the effects on the tryptophan-producing strains were evaluated.

In order to evaluate the titer, each strain was inoculated by a platinum loop and cultured overnight on LB solid medium. Then, one platinum loop of each strain was inoculated into 25 mL of glucose-containing medium, the composition of the medium is shown in Table 4 below. After inoculation, each strain was incubated at 37° C. and 200 rpm for 48 hours. The results are shown in Table 5 below. All the results were recorded as the average of three flask results.

TABLE 4

| Composition | Concentration (per liter) |
|---|---|
| Glucose | 60 g |
| $K_2HPO_4$ | 1 g |
| $(NH_4)_2SO_4$ | 10 g |
| NaCl | 1 g |
| $MgSO_4 \cdot H_2O$ | 1 g |
| Sodium citrate | 5 g |
| Yeast extract | 2 g |
| Calcium carbonate | 40 g |
| Sodium citrate | 5 g |
| Phenylalanine | 0.15 g |
| Tyrosine | 0.1 g |
| pH | 6.8 |

TABLE 5

| Vector | | OD | Glucose consumption (g/L)* | L-tryptophan (g/L)** | Anthranilate (mg/L)** |
|---|---|---|---|---|---|
| pCL | pBAC | | | | |
| pCL1920 | pCC1BAC | 13.5 | 53.0 | 7.0 | 1005 |
| pCL-Ptrp_trpEDCBA | pBAC-Ptrp_trpEDCBA | 14.0 | 52.1 | 7.2 | 1053 |
| | pBAC-DtrpL_trpEDCBA | 14.2 | 51.0 | 7.5 | 1157 |
| | pBAC-Dtrp_att-trpEDCBA | 13.8 | 52.6 | 7.1 | 1263 |
| pCL-DtrpL_trpEDCBA | pBAC-Ptrp_trpEDCBA | 13.9 | 50.0 | 7.5 | 1170 |
| | pBAC-DtrpL_trpEDCBA | 13.7 | 51.6 | 7.3 | 1290 |
| | pBAC-Dtrp_att-trpEDCBA | 13.6 | 49.8 | 7.8 | 1485 |
| pCL-Ptrp_att-trpEDCBA | pBAC-Ptrp_trpEDCBA | 13.8 | 49.8 | 7.5 | 1358 |
| | pBAC-DtrpL_trpEDCBA | 13.1 | 47.6 | 7.6 | 1501 |
| | pBAC-Dtrp_att-trpEDCBA | 12.7 | 45.3 | 7.5 | 1853 |
| pCL-Ptrp_trpEDCBA | pBAC-Ptrp_trpDCBA | 14.2 | 52.1 | 7.5 | 950 |
| | pBAC-DtrpL_trpDCBA | 14.6 | 51.3 | 7.2 | 813 |
| | pBAC-Dtrp_att-trpDCBA | 14.3 | 52.7 | 7.1 | 687 |
| pCL-DtrpL_trpEDCBA | pBAC-Ptrp_trpDCBA | 13.9 | 50.6 | 7.5 | 953 |
| | pBAC-DtrpL_trpDCBA | 13.7 | 51.7 | 7.6 | 852 |
| | pBAC-Dtrp_att-trpDCBA | 13.6 | 51.3 | 7.7 | 715 |
| pCL-Dtrp_att-trpEDCBA | pBAC-Ptrp_trpDCBA | 13.2 | 51.6 | 8.0 | 1085 |
| | pBAC-DtrpL_trpDCBA | 13.9 | 50.9 | 8.6 | 867 |
| | pBAC-Dtrp_att-trpDCBA | 13.5 | 51.2 | 9.5 | 783 |

*measured at 33 hours
**measured at 48 hours

As can be seen from the results in Table 5 above, in the case in which the parent strain E. coli KCCM10812P was transformed with a combination of various vectors, if only the tryptophan operon was continuously enhanced, no positive effect on the production yield of tryptophan appeared while anthranilate accumulated. On the contrary, it appears that the strain modified by enhancing the operon using the pCL vector and enhancing trpDCBA using the pBAC vector showed a positive effect on the production yield of tryptophan together with a decrease in the accumulation of anthranilate, compared to the strain in which only tryptophan operon was enhanced. Thus, it was confirmed that a decrease in the accumulation of anthranilate is an effective way to increase the production yield of L-tryptophan in tryptophan-producing strains.

Example 10

Construction of Strain Wherein the Copy Number of the Tryptophan Biosynthetic Gene Cluster trpDCBA in the Chromosome was Increased and the Accumulation of Anthranilate Decreased Based on the results of Example 9, in order to increase the copy number of the tryptophan biosynthetic gene cluster trpDCBA in the chromosome, a vector was constructed.

Specifically, pCL-Dtrp_att-trpDCBA described in Example 5 was cleaved with the restriction enzymes EcoRI and BamHI to obtain Dtrp_att-trpDCBA, and then ligated with pINT17E treated with the same restriction enzymes, thereby obtaining pINT17E-Patt-trpDCBA. In order to introduce pINT17E-Patt-trpDCBA into the tryptophan-producing parent strain E. coli KCCM10812P to increase the copy number of the tryptophan biosynthetic gene cluster trpDCBA, pKD46 that is used in the one-step inactivation method (developed by Datsenko K A et al.), a mutagenesis technique using lambda red recombinase, according to Example 6. As a marker for confirming insertion into the genes, the chloramphenicol-resistant gene of pUCprmfmloxC was used. Specifically, the parent strain, in which pKD46 was introduced, transformed with pINT17E-Patt-trpDCBA, and then cultured at 37° C. for 1-2 days to obtain colonies. To confirm whether pINT17E-Patt-trpDCBA was correctly inserted into the chromosome of the obtained colonies, about 2000-bp fragment was amplified by PCR using primers 21 and 22.

```
Primer 21:
                               (SEQ ID NO: 31)
5' TATTTGCTGTCACGAGCAGG 3';

Primer 22:
                               (SEQ ID NO: 32)
5' AGTTCCGGCATACAACCGGCTT 3'.
``` pKD46 was removed from the primary recombinant strain having chloramphenicol resistance, and then pJW168 plasmid was introduced to remove the chloramphenicol marker gene from the strain (Gene, (2000) 247, 255-264). An about 5000-bp amplification product obtained by PCR using primers 23 and 24, and an about 6500-bp amplification product obtained by PCR using primers 25 and 26, it demonstrated that trpDCBA is continuously place following the tryptophan operon which endogenously place on the chromosome. This strain was named "KCCM10812P/trpDCBA".

```
Primer 23:
                               (SEQ ID NO: 33)
5' TAATACGACTCACTATAGGG 3';

Primer 24:
                               (SEQ ID NO: 34)
5' CTGTTGGGCGGAAAAATGAC 3';

Primer 25:
                               (SEQ ID NO: 35)
5' TGATCGCCAGGGTGCCGACG 3';

Primer 26:
                               (SEQ ID NO: 36)
5' CCCTATAGTGAGTCGTATTA 3'.
```

In order to additionally insert one copy into the above-prepared strain in which the copy number of trpDCBA was increased, pKD46 was introduced into the above-prepared KCCM10812P/trpDCBA strain. Then the pINT17E-Patt-trpDCBA vector was introduced into KCCM10812P/trpDCBA/pKD46, thereby constructing a strain having two copies of trpDCBA inserted into the chromosome. This constructed strain was named "KCCM10812P/2trpDCBA". This strain was deposited with the Korean Culture Center of Microorganisms (361-221, Hongje 1-dong, Seodaemun-gu, Seoul, Korea), an international depository authority, on Dec. 29, 2011 under the accession number KCCM11246P.

Example 11

Examination of Effect of L-Tryptophan-Producing Strain Having Increased Activities of Proteins that are Encoded by the Tryptophan Biosynthetic Gene Cluster trpDCBA According to the method described in Example 10, the titer of KCCM10812P/trpDCBA was evaluated using glucose as a carbon source. The KCCM10812P/trpDCBA was obtained by further introducing trpDCBA into the tryptophan-producing strain E. coli KCCM10812P to enhance the activities of some enzymes of tryptophan biosynthesis pathway.

To evaluate the titer, the strain was inoculated by a platinum loop and cultured overnight on LB solid medium. Then, one platinum loop of the strain culture was inoculated into 25 ml of a flask titer medium, the composition of the medium is shown in Table 4 above. After inoculation, the strain was cultured at 37° C. and 200 rpm for 48 hours. The results are shown in Table 6 below. All the results were recorded as the average of three flask results.

TABLE 6

| Strain | OD | Glucose consumption (g/L)* | L-tryptophan (g/L)** | Anthranilate (mg/L) |
|---|---|---|---|---|
| KCCM10812P | 14.0 | 54.0 | 7.2 | 1020 |
| KCCM10812P/ trpDCBA | 14.5 | 54.5 | 7.9 | 630 |
| KCCM10812P/2 trpDCBA | 13.3 | 55.2 | 8.2 | 320 |

*measured at 33 hours
**measured at 48 hours

As can be seen in Table 6 above, when one copy of the tryptophan biosynthetic gene cluster trpDCBA was inserted into the chromosome, the concentration of anthranilate decreased by 39% compared to that in the parent strain.

however two copies were inserted into the chromosome, the concentration of anthranilate decreased by 69% compared to that in the parent strain.

In addition, the concentrations of L-tryptophan in the two strains increased by 10% and 13%, respectively. As shown in Table 6 above, when the copy number of trpDCBA was increased, the consumption rate of glucose slightly decreased in some cases, but the enhancement of the tryptophan biosynthetic gene cluster has positive effects on an increase in the concentration of L-tryptophan and a decrease in the concentration of anthranilate.

While the present invention has been described with reference to the particular illustrative embodiments, those skilled in the art to which the present invention pertains can understand that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

Accession Number

Depository authority: Korean Culture Center of Microorganisms(international)

Accession Number: KCCM11246P

Deposition date: Dec. 29, 2011

The invention claimed is:

1. A recombinant microorganism of the genus *Escherichia* having an enhanced L-tryptophan productivity compared to the L-tryptophan productivity of a corresponding wild-type *Escherichia* microorganism, wherein the recombinant microorganism has a modification to a chromosomal tryptophan operon, wherein the modification is a deletion of part or all of the nucleotide sequence of SEQ ID NO: 2 in an expression regulatory region comprising the nucleotide sequence of SEQ ID NO: 1, wherein the recombinant microorganism is transformed with tryptophan operon genes trpD, trpC, trpB, and trpA for increased expression of said tryptophan operon genes as compared to the corresponding wild-type *Escherichia* microorganism, and wherein the recombinant microorganism does not have increased expression of a trpE gene or increased activity of anthranilate synthase encoded by the trpE gene as compared to the corresponding wild-type *Escherichia* microorganism.

2. The recombinant microorganism according to claim 1, wherein the recombinant microorganism has an additional modification to the chromosomal tryptophan operon, wherein the modification is a deletion of part or all of the nucleotide sequence of SEQ ID NO: 3 in the expression regulatory region comprising the nucleotide sequence of SEQ ID NO: 1.

3. The recombinant microorganism according to claim 2, wherein the trpD gene encodes a polypeptide comprising the amino acid sequence of SEQ ID NO:37, the trpC gene encodes a polypeptide comprising the amino acid sequence of SEQ ID NO:38, the trpB gene encodes a polypeptide comprising the amino acid sequence of SEQ ID NO:39, and the trpA gene encodes a polypeptide comprising the amino acid sequence of SEQ ID NO:40.

4. The recombinant microorganism according to claim 1, wherein the recombinant microorganism is an *Escherichia coli* strain.

5. A method for producing L-tryptophan, comprising culturing the recombinant microorganism of claim 1 under conditions suitable for the production of L-tryptophan.

6. The method according to claim 5, wherein the recombinant microorganism has a further modification to a chromosomal tryptophan operon, wherein the modification is a deletion of part or all of the nucleotide sequence of SEQ ID NO: 3 in the expression regulatory region comprising the nucleotide sequence of SEQ ID NO: 1.

7. The method according to claim 5, wherein the recombinant microorganism is an *Escherichia coli* strain.

* * * * *